(12) United States Patent
Kulbrandstad et al.

(10) Patent No.: US 11,815,501 B2
(45) Date of Patent: Nov. 14, 2023

(54) ONLINE MONITORING OF PRODUCTION PROCESSES USING ELECTRON PARAMAGNETIC RESONANCE (EPR)

(71) Applicant: MICROSILICON, INC., Katy, TX (US)

(72) Inventors: Omar Kulbrandstad, Katy, TX (US);
Aydin Babakhani, Houston, TX (US);
Manuel Godoy, Houston, TX (US);
John Lovell, Houston, TX (US)

(73) Assignee: MICROSILICON, INC., Katy, TX (US)

( * ) Notice: Subject to any disclaimer, the term of this patent is extended or adjusted under 35 U.S.C. 154(b) by 0 days.

(21) Appl. No.: 17/929,885

(22) Filed: Sep. 6, 2022

(65) Prior Publication Data
US 2023/0127803 A1    Apr. 27, 2023

Related U.S. Application Data

(63) Continuation of application No. 16/952,826, filed on Nov. 19, 2020, now Pat. No. 11,525,816, which is a (Continued)

(51) Int. Cl.
*G01R 33/24* (2006.01)
*G01N 33/00* (2006.01)
(Continued)

(52) U.S. Cl.
CPC ......... *G01N 33/0031* (2013.01); *E21B 49/08* (2013.01); *G01N 24/10* (2013.01);
(Continued)

(58) Field of Classification Search
CPC .............. G01R 33/543; G01R 33/5608; G01R 33/4828; G01R 33/3415; G01R 33/283;
(Continued)

(56) References Cited

U.S. PATENT DOCUMENTS 4,803,624 A    2/1989  Pilbrow et al.
4,888,554 A    12/1989 Hyde et al.
(Continued)

FOREIGN PATENT DOCUMENTS

WO         9859220 A2    12/1998
WO    WO-9859220 A2    12/1998
(Continued)

OTHER PUBLICATIONS

Chzhan, M., et al., "A Tunable Reentrant Resonator with Transverse Orientation of Electric Field for in Vivo EPR Spectroscopy," Journal of Magnetic Resonance 137, 373-378 (1999).
(Continued)

*Primary Examiner* — Jermele M Hollington
*Assistant Examiner* — Taqi R Nasir
(74) *Attorney, Agent, or Firm* — Patterson + Sheridan, LLP

(57) ABSTRACT

Certain aspects of the present disclosure provide methods and apparatus for closed-loop control of a system using one or more electron paramagnetic resonance (EPR) sensors located on-site. With such EPR sensors, a change can be applied to the system, the EPR sensors can measure the effect(s) of the change, and then adjustments can be made in real-time. This feedback process may be repeated continuously to control the system.

38 Claims, 15 Drawing Sheets

Related U.S. Application Data continuation of application No. 15/891,034, filed on Feb. 7, 2018, now Pat. No. 10,859,549.

(60) Provisional application No. 62/463,810, filed on Feb. 27, 2017, provisional application No. 62/455,933, filed on Feb. 7, 2017.

(51) Int. Cl.

| | |
|---|---|
| *E21B 49/08* | (2006.01) |
| *G01R 33/60* | (2006.01) |
| *G01V 3/26* | (2006.01) |
| *G01R 33/44* | (2006.01) |
| *G01R 33/36* | (2006.01) |
| *G01V 3/32* | (2006.01) |
| *G01N 24/10* | (2006.01) |

(52) U.S. Cl.
CPC ......... *G01R 33/24* (2013.01); *G01R 33/3607* (2013.01); *G01R 33/448* (2013.01); *G01R 33/60* (2013.01); *G01V 3/265* (2013.01); *G01V 3/32* (2013.01); *E21B 49/0875* (2020.05)

(58) Field of Classification Search
CPC ........ G01R 33/307; G01R 33/60; G01V 3/32; E21B 49/08; E21B 2049/085; G01N 24/10
See application file for complete search history.

(56) References Cited

U.S. PATENT DOCUMENTS

| | | | |
|---|---|---|---|
| 5,233,303 A | | 8/1993 | Bales et al. |
| 6,051,535 A | | 4/2000 | Bilden et al. |
| 6,268,727 B1 | * | 7/2001 | King ........................ G01F 1/716 324/306 |
| 6,346,813 B1 | | 2/2002 | Kleinberg |
| 6,573,715 B2 | | 6/2003 | King et al. |
| 7,683,613 B2 | | 3/2010 | Freedman et al. |
| 7,868,616 B2 | | 1/2011 | White et al. |
| 8,125,224 B2 | | 2/2012 | White et al. |
| 8,210,826 B2 | | 7/2012 | Freeman |
| 8,212,563 B2 | | 7/2012 | White et al. |
| 8,310,235 B1 | | 11/2012 | Gerald, II et al. |
| 8,829,904 B2 | | 9/2014 | White et al. |
| 9,103,261 B1 | | 8/2015 | White et al. |
| 9,689,954 B2 | | 6/2017 | Yang et al. |
| 2001/0028247 A1 | | 10/2001 | King et al. |
| 2002/0140425 A1 | * | 10/2002 | Prammer ............. G01R 33/307 324/306 |
| 2008/0173447 A1 | | 7/2008 | Da Silva et al. |
| 2011/0040501 A1 | * | 2/2011 | Martin ....................... G01F 1/74 702/45 |
| 2012/0087867 A1 | | 4/2012 | McCamey et al. |
| 2012/0223715 A1 | | 9/2012 | Park et al. |
| 2012/0267115 A1 | | 10/2012 | Brown et al. |
| 2013/0093424 A1 | | 4/2013 | Blank et al. |
| 2013/0257431 A1 | | 10/2013 | Tseitlin et al. |
| 2014/0097842 A1 | | 4/2014 | Yang et al. |
| 2015/0097561 A1 | | 4/2015 | Desmulliez et al. |
| 2015/0185255 A1 | | 7/2015 | Eaton et al. |
| 2015/0185299 A1 | | 7/2015 | Rinard et al. |
| 2016/0223478 A1 | | 8/2016 | Babakhani et al. |
| 2017/0226973 A1 | | 8/2017 | Blizard et al. |

FOREIGN PATENT DOCUMENTS

| | | |
|---|---|---|
| WO | 2016/187300 A1 | 11/2016 |
| WO | WO-2016/187300 A1 | 11/2016 |

OTHER PUBLICATIONS

J. A. Weil and J. R. Bolton, Electron Paramagnetic Resonance: Elementary Theory and Practical Applications, 2nd Ed., Hoboken, NJ: John Wiley & Sons, 2007, pp. 33-35.

Gilbert et al., Electron Paramagnetic Resonance, vol. 20, The Royal Society of Chemistry, Cambridge UK 2007.

A. Schweiger and G. Jeschke, Principles of Pulse Electron Paramagnetic Resonance, Oxford University Press, 2001.

G.R. Eaton, S.S. Eaton, D.P. Barr, and R.T. Weber, Quantitative EPR, Vienna: Springer, 2010.

S. Petryakov et al., "Single Loop-MultiGap Resonator for Whole Body EPR Imaging of Mice at 1.2 GHz," Journal of Magnetic Resonance, v188(1), pp. 1-13 (Sep. 2007).

H. Yokoyama and T. Yoshimura, "Combining a magnetic field modulation coil with a surface-coil-type EPR resonator," Applied Magnetic Resonance, vol. 35, Issue 1, pp. 127-128 (Nov. 2008).

Sundramoorthy et al., "Orthogonal Resonators for Pulse In Vivo Electron Paramagnetic Imaging at 250MHz," Journal Magnetic Resonance, vol. 240, pp. 45-51 (Mar. 2014).

"Measurement of Complex Permittivity and Permeability through a Cavity Perturbation Measurement," Master's Thesis in Applied Physics by Tomas Rydholm, Chalmers University of Technology, Sweden, 2015.

Mamin, G. V., et al., "Toward the Asphaltene Structure by Electron Paramagnetic Resonance Relaxation Studies at High Fields (3.4 T)," Energy Fuels, 2016, 30 (9), pp. 6942-6946.

Biktagirov et al., "Electron Paramagnetic Resonance Study of Rotational Mobility of the Vanadyl Porphyrin Complexes in Crude Oil Asphaltenes: Probing the Effect of the Thermal Treatment of Heavy Oils," Energy & Fuels, 2014, 28, pp. 6683-6687.

Tukhvatullina, A. Z,, et al., "Supramolecular Structures of Oil Systems as the Key to Regulation of Oil Behavior," Petroleum & Environmental Biotechnology, <http://dx.doi.org/10.4172/2157-7463.1000152> (2013).

Crude Oil Emulsions—Composition, Stability, and Characterization, Edited by Manar El-Sayed Abdel, published by Intech, 2012, Croatia. ISBN 978-953-51-0220-5.

Marcela Espinosa P., et al., "Electron Spin Resonance and Electronic Structure of Vanadyl-Porphyrin in Heavy Crude Oils," Inorg. Chem., 2001, 40, pp. 4543-4549.

Teh Fu Yen, et al., "Investigation of the Nature of Free Radicals in Petroleum Asphaltenes and Related Substances by Electron Spin Resonance," Analytical Chemistry, 1962, 34(6), pp. 694-700.

L. Montenari, et al., "Asphaltene Radicals and their Interaction with Molecular Oxygen: an EPR Probe of their Molecular Characteristics and Tendency to Aggregate," Appl. Magn. Reson., 1998, 14, pp. 81-82.

K.J. Leontaritis, "Asphaltene Deposition: A Comprehensive Description of Problem Manifestations and Modeling Approaches," SPE-18892-MS, Mar. 1989.

Adel M. Elsharkawy, et al., "Characterization of Asphaltenes and Resins Separated from Water-in-Oil Emulsions," Journal Petroleum Science and Technology, vol. 26, 2008—Issue 2, 22 Pages.

Sanjay Misra, et al., "Successful Asphaltene Cleanout Field Trial in On-Shore Abu Dhabi Oil Fields," SPE 164175-MS, Mar. 2013, pp. 1-5.

Cole, K. S. et al., "Dispersion and Absorption in Dielectrics," J. Appl. Phys., 9, 341-351 (1941).

Freed, J. H., et al., "Theory of Linewidths in Electron Spin Resonance Spectra," The Journal of Chemical Physics, vol. 39, (1963), pp. 326-348.

Lesaint, C., et al., "Properties of Asphaltene Solutions: Solvency Effect on Conductivity," Energy Fuels, 27 (1), (2013), pp. 75-81.

Goual, L., "Impedance Spectroscopy of Petroleum Fluids at Low Frequency," Energy and Fuels, 23, (2009), pp. 2090-2094.

Penzes, S., et al., "Electrical conductivities of bitumen fractions in non-aqueous solvents," Fuel, 53, (1974), pp. 192-197.

Fotland, P., "Conductivity of Asphaltenes," Structure and Dynamics of Asphaltenes, Plenum: New York, 1998.

Sheu, E. Y., et al., "Frequency-dependent conductivity of Utah crude oil asphaltene and deposit," Energy Fuels, 18, (2004), pp. 1531-1534.

(56) References Cited

OTHER PUBLICATIONS

Sheu, E. Y., et al., "Asphaltene self-association and precipitation in solvents and AC conductivity measurements," Asphaltenes, Heavy Oils and Petroleomics, Springer: New York, 2007, pp. 259-260.
Sheu, E. Y., et al., "A dielectric relaxation study of precipitation and curing of Furrial crude oil," Fuel, vol. 85, (2006) pp. 1953-1959.
S. Kokal et al., "Asphaltene Precipitation in a Saturated Gas-Cap Reservoir", Society of Petroleum Engineers Inc., SPE 89967 (2004) pp. 1-9.
International Search Report and Written Opinion dated Jun. 8, 2018, corresponding to Application No. PCT/US2018/017224.

\* cited by examiner

ONLINE MONITORING OF PRODUCTION PROCESSES USING ELECTRON PARAMAGNETIC RESONANCE (EPR)

CLAIM OF PRIORITY

This application is a continuation of co-pending U.S. patent application Ser. No. 16/952,826, entitled "Online Monitoring of Production Processes Using Electron Paramagnetic Resonance (EPR)" and filed Nov. 19, 2020, which is a continuation of U.S. patent application Ser. No. 15/891,034, filed Feb. 7, 2018 (now U.S. Pat. No. 10,859,549), which claims the benefit of U.S. Provisional Patent Application No. 62/455,933, filed Feb. 7, 2017, and the benefit of U.S. Provisional Patent Application No. 62/463,810, filed Feb. 27, 2017, all of which are herein incorporated by reference in their entireties.

BACKGROUND

Field of the Disclosure

The present disclosure generally relates to electron paramagnetic resonance (EPR) and, more specifically, to applications of EPR sensors for hydrocarbon recovery operations.

Relevant Background

Electron paramagnetic resonance (EPR), also referred to as electron spin resonance (ESR), is a spectroscopic and imaging technique that is capable of providing quantitative information regarding the presence and concentration of a variety of paramagnetic species within a sample under test. The valence electrons of a paramagnetic species possess unpaired spin angular momentum and, thus, have net magnetic moments that tend to align along an externally applied magnetic field. This alignment process is known as paramagnetization. EPR is a measurement technique that relies on the external manipulation of the direction of this electron paramagnetization, also referred to as a net electronic magnetic moment. In a typical EPR study, a polarizing static magnetic field $B_0$ (also referred to as a DC magnetic field) is applied to a sample to align the magnetic moments of the electrons along the direction of the magnetic field $B_0$. Then, a high-frequency oscillating magnetic field $B_1$, often referred to as the transverse magnetic field or the radio frequency (RF) magnetic field, is applied along a direction that is perpendicular to the polarizing field $B_0$. Usually, the oscillating field $B_1$ is generated using a microwave resonator (fed via a coil or a transmission line) and is designed to excite the unpaired electrons by driving transitions between the different angular momentum states of the unpaired electron(s).

EPR technology is based on the interaction of these electron spins with the applied RF (e.g., microwave) electromagnetic fields in the presence of the external static (DC) magnetic field. EPR data provides valuable information about electronic structures and spin interactions in paramagnetic materials. EPR has found wide-ranging applications in various science and engineering technology areas, such as studying chemicals involving free radicals or transition metal ions.

EPR responses to oilfield fluids have been studied by many authors. For example, in Mamin, G. V., et al., "Toward the Asphaltene Structure by Electron Paramagnetic Resonance Relaxation Studies at High Fields (3.4 T)," *Energy Fuels*, 2016, 30 (9), pp 6942-6946, the authors studied a series of 12 asphaltene samples extracted from heavy oils and the oxidized bitumen of different origin using high-frequency W-band (94 GHz) pulsed EPR spectroscopy. The authors effectively measured the distance between free-radical and vanadyl components of the asphaltene and inferred mechanisms on how the vanadyl can participate in construction of the asphaltene aggregates via the intermolecular interactions. Other publications on asphaltene EPR response include Biktagirov et al., "Electron Paramagnetic Resonance Study of Rotational Mobility of the Vanadyl Porphyrin Complexes in Crude Oil Asphaltenes: Probing the Effect of the Thermal Treatment of Heavy Oils," *Energy & Fuels*, 2014, 28, pp 6683-6687; Tukhvatullina, A. Z, et al., "Supramolecular Structures of Oil Systems as the Key to Regulation of Oil Behavior," *Petroleum & Environmental Biotechnology*, http://dx.doi.org/10.4172/2157-7463.1000152 (2013); Crude Oil Emulsions—Composition, Stability, and Characterization, Edited by Manar El-Sayed Abdel, published by Intech, 2012, Croatia. ISBN 978-953-51-0220-5; Marcela Espinosa P., et al., "Electron Spin Resonance and Electronic Structure of Vanadyl-Porphyrin in Heavy Crude Oils," *Inorg. Chem.*, 2001, 40, pp. 4543-4549; Teh Fu Yen, et al., "Investigation of the Nature of Free Radicals in Petroleum Asphaltenes and Related Substances by Electron Spin Resonance," *Analytical Chemistry*, 1962, 34(6), pp. 694-700; and L. Montenari, et al., "Asphaltene Radicals and their Interaction with Molecular Oxygen: an EPR Probe of their Molecular Characteristics and Tendency to Aggregate," *Appl. Magn. Reson.*, 1998, 14, pp. 81-100. All of the above papers are herein incorporated by reference in their entireties. As a general summary, the authors demonstrate that significant information about crude oil and asphaltene can be gleaned from the EPR response. This information can be used to help mitigate asphaltene deposition within a well, which is a multibillion dollar industry problem. All of these papers use laboratory reference EPR spectrometers. They do not anticipate taking EPR data in real-time using wellsite equipment connected to the production flow.

U.S. Pat. No. 6,573,715 to King et al., entitled "Porosity and Permeability Measurement of Underground Formations Containing Crude Oil, Using EPR Response Data" and issued Jun. 3, 2003, describes the use of an in-well EPR apparatus. Given a correlation between volume of oil and paramagnetic response, then the in-well tool measures the EPR paramagnetic response and hence the volume of crude oil in the rock being sensed by the tool as it traverses the wellbore. U.S. Pat. No. 6,346,813 to Kleinberg, entitled "Magnetic Resonance Method for Characterizing Fluid Samples Withdrawn from Subsurface Formations" and issued Feb. 12, 2002 (hereinafter "Kleinberg '813"), considers the case of flowing pressurized fluid samples from a wellbore into a downhole tool and expelling that fluid back into the wellbore. In this application, the EPR data is used to identify contaminants, such as an oil-based drilling mud versus crude oil flowing from the reservoir. In neither of these patents do the authors assume that the oil is flowing freely to the surface.

More recent EPR spectrometer developments, such as those described in U.S. Pat. No. 9,689,954 to Yang et al., entitled "Integrated Electron Spin Resonance Spectrometer" and issued Jun. 27, 2017, permit using EPR sensors in applications that were previously unachievable due to size constraints. Other patents disclosing smaller devices include U.S. Pat. No. 8,212,563 to White et al., entitled "Method and Apparatus for In-situ Measurement of Soot by Electron Spin Resonance (ESR) Spectrometry" and issued Jul. 3, 2012;

U.S. Pat. No. 8,829,904 to White et al., entitled "Method of and Apparatus for In-situ Measurement of Degradation of Automotive Fluids and the Like by Micro-electron Spin Resonance (ESR) Spectrometry" and issued Sep. 9, 2014; U.S. Pat. No. 7,868,616 to White et al., entitled "Method of and Apparatus for In-situ Measurement of Changes in Fluid Composition by Electron Spin Resonance (ESR) Spectrometry" and issued Jan. 11, 2011; and U.S. Pat. No. 5,233,303 to Bales et al., entitled "Portable Dedicated Electron Spin Resonance Spectrometer" and issued Aug. 3, 1993. The entire contents of these five patents are herein incorporated by reference.

EPR data has been proposed to guide decision processes. For example, Kleinberg '813 proposes to use the EPR data to identify when uncontaminated reservoir crude oil has fully displaced well fluid contaminated by mud particles, and at that point open a valve to divert the crude to a downhole sample chamber. U.S. Pat. No. 9,103,261 to White et al., entitled "Device and Method for Adjusting Dosage of Fuel Additive Based on In-Situ Measurement of Additive and Containment Concentration" and issued Aug. 11, 2015, discloses a method to miscibly combine two fluids, one with contaminants, where the concentration of the second fluid is determined by the EPR estimation of the contaminants in the first. These patents do not anticipate multiphase fluid flow through the device.

As reservoirs deplete due to oilfield extraction, the quality of a crude oil will change. As a general statement, one can expect over time an increase in the percentages of dissolved gas and water in the crude as it exits the reservoir. As that oil returns to the surface, the pressure seen by the oil decreases, the dissolved gas will expand, and once the pressure drops to the bubble-point, then gas will come out of solution. Above that point, the oil and gas will flow as separate phases. During early production any formation water might flow with the oil, but it is very common to see the amount of water increase over time. Enhanced recovery operations will increase that amount of produced water yet further. As water (or mixes of water and gas) are injected into dedicated wells, then that water will displace oil from some pore volumes, but that same water will also start to appear in the producing wells. For wells that have been under enhanced recovery for many years (such as some Permian fields near Midland in Texas or those under water flood in Oman), then the produced water can easily exceed 90%.

It is known that in multiphase flow, the immiscible fluids may traverse in different flow regimes (e.g., bubble flow, slug flow, and emulsion flow for two liquids and bubble flow, dispersed bubble flow, plug flow, slug flow, froth flow, mist flow, churn flow, and annular flow for gas-liquid combinations). It is also known that for some of these flow regimes, turbulizers can be included in the tubular to make downstream cross-sections of the pipe more representative of the average flow (e.g., for sampling). For slug flow, however, turbulizers are less useful: the first fluid will not become blended with the second. Rather, the two fluids will stay as separate components travelling along the wellbore. Such a scenario is not uncommon for applications of enhanced oil recovery when the wellhead may see many feet of water, followed by a few feet of oil/water, and then many more feet of water. Another common scenario for heavy oil production is that the produced fluid consists of a thick emulsion of oil with 10-30% water. It is also common that the water will include dissolved metal ions that increase the conductivity of the water (and so decrease a measured EPR signal). In these and similar scenarios, it becomes challenging to take a real-time measurement of the EPR properties of the oil.

Applications for real-time EPR measurements of crude oil were disclosed, for example, in U.S. Patent Publication No. 2016/0223478 to Babakhani et al., entitled "EPR Systems for Flow Assurance and Logging" and filed Sep. 25, 2014 (hereinafter "Babakhani '478"), which is herein incorporated by reference in its entirety. Babakhani '478 describes that the EPR signal can be converted into percentages of asphaltenes, resins, waxes, and other components of crude oil. Another patent herein incorporated by reference in its entirety is U.S. Pat. No. 8,125,224 to White et al., entitled "Method of and Apparatus for In-Situ Measurement of Degradation of Automotive Fluids and the Like by Micro-Electron Spin Resonance (ESR) Spectrometry" and issued Feb. 28, 2012, describes that the ESR signal can also be combined with other measurements, such as a measurement of viscosity, conductivity, chromatic modulation, x-ray fluorescence, infrared, and dielectric permittivity. Permittivity data is known to be useful when considering fluids with polar components, such as asphaltene particles inside crude oil. Useful methodologies can be found, for example, in K. J. Leontaritis, "Asphaltene Deposition: A Comprehensive Description of Problem Manifestations and Modeling Approaches," SPE-18892-MS, March 1989 and Adel M. Elsharkawy, et al., "Characterization of Asphaltenes and Resins Separated from Water-in-Oil Emulsions," *Journal Petroleum Science and Technology*, Volume 26, 2008—Issue 2. These two papers are herein incorporated by reference in their entireties.

Many different techniques for injecting chemicals into a well are known in the industry. For example, U.S. Pat. No. 8,210,826 to Freeman, entitled "Controlled Liquid Injection and Blending Apparatus" and issued Jul. 3, 2012 (hereinafter "Freeman '826"), discloses one technique where the chemicals take the form of an additive liquid to be added to a base liquid at a ratio driven according to a control mechanism that in turn is based on measurement of temperature, pressure, and additive concentration. Freeman '826 does not disclose the option of measuring the chemical effect of that injection on a third fluid flowing from a wellbore. Nonadditive injection techniques are also common in the oil industry. In one example, the chemical mixture is blended appropriately before pouring into a tank, and then a control mechanism is used to meter the rate at which that chemical is injected (e.g., to be pumped down a chemical injection line as described in U.S. Pat. No. 6,051,535 to Bilden et al., entitled "Asphaltene Adsorption Inhibition Treatment" and issued Apr. 18, 2000).

At its simplest, the injection could take the form of a bullheading of solvent directly into the well, such as described in Sanjay Misra, et al., "Successful Asphaltene Cleanout Field Trial in On-Shore Abu Dhabi Oil Fields," SPE 164175-MS, March 2013. In this case the control feedback loop is completely non-automated: it consists of waiting for a few months to see if production is at desired rate and if not then performing another bullhead, where the parameters to be adjusted would be the chemical constituency, the amount of chemical, and the soak duration. This last non-automated feedback can be described as reactive, instead of proactive.

Accordingly, there is a need to be able to take EPR measurements at the wellsite while fluids are flowing, extract properties of that fluid, and use that information to drive closed-loop control of a fluid management system.

SUMMARY

Certain aspects of the present disclosure generally relate to closed-loop control of a system utilizing electron paramagnetic resonance (EPR).

Certain aspects of the present disclosure provide a method of sensing a multiphase fluid. The method generally includes extracting at least one characteristic of at least one of a first phase or a second phase in the multiphase fluid in a flowing system, performing EPR spectroscopy on at least a portion of the multiphase fluid to generate an EPR spectrum, and determining at least one property of the multiphase fluid based on the EPR spectrum and the at least one characteristic.

Certain aspects of the present disclosure provide a non-transitory computer-readable medium storing instructions that, when executed on a processor, perform operations for sensing a multiphase fluid. The operations generally include extracting at least one characteristic of at least one of a first phase or a second phase in the multiphase fluid in a flowing system, performing EPR spectroscopy on at least a portion of the multiphase fluid to generate an EPR spectrum, and determining at least one property of the multiphase fluid based on the EPR spectrum and the at least one characteristic.

Certain aspects of the present disclosure provide a system for sensing a multiphase fluid configured to flow in the system. The system generally includes at least one sensor configured to extract at least one characteristic of at least one of a first phase or a second phase in the multiphase fluid, an EPR spectrometer configured to perform EPR spectroscopy on at least a portion of the multiphase fluid to generate an EPR spectrum, and at least one processor coupled to the at least one sensor and the EPR spectrometer and configured to determine at least one property of the multiphase fluid based on the EPR spectrum and the at least one characteristic.

Certain aspects of the present disclosure provide a method of sensing a fluid in a flowing system. The method generally includes performing EPR spectroscopy, using an EPR spectrometer, on at least a portion of the fluid to generate an EPR spectrum; determining at least one property of the fluid based on the EPR spectrum; and calculating a deviation of a current value of the at least one property from a baseline value of the at least one property.

Certain aspects of the present disclosure provide a non-transitory computer-readable medium storing instructions that, when executed on a processor, perform operations for sensing a fluid in a flowing system. The operations generally include performing EPR spectroscopy on at least a portion of the fluid to generate an EPR spectrum, determining at least one property of the fluid based on the EPR spectrum, and calculating a deviation of a current value of the at least one property from a baseline value of the at least one property.

Certain aspects of the present disclosure provide a system for sensing a fluid configured to flow in the system. The system generally includes an EPR spectrometer configured to perform EPR spectroscopy on at least a portion of the fluid to generate an EPR spectrum and at least one processor coupled to the EPR spectrometer. The at least one processor is configured to determine at least one property of the fluid based on the EPR spectrum and to calculate a deviation of a current value of the at least one property from a baseline value of the at least one property.

Certain aspects of the present disclosure provide a method of monitoring multiple flow systems using EPR. The method generally includes performing EPR spectroscopy on a fluid in each of a first group of flow systems to generate a plurality of EPR spectrums and determining, for each of the first group of flow systems, at least one property of the fluid based on the EPR spectrum associated with the flow system.

Certain aspects of the present disclosure provide a non-transitory computer-readable medium storing instructions that, when executed on a processor, perform operations for monitoring multiple flow systems using EPR. The operations generally include performing EPR spectroscopy on a fluid in each of a first group of flow systems to generate a plurality of EPR spectrums and determining, for each of the first group of flow systems, at least one property of the fluid based on the EPR spectrum associated with the flow system.

Certain aspects of the present disclosure provide a system for monitoring multiple flow systems using EPR. The system generally includes a plurality of EPR spectrometers and at least one processor coupled to the plurality of EPR spectrometers. The plurality of EPR spectrometers are generally configured to perform EPR spectroscopy on a fluid in each of a first group of flow systems to generate a plurality of EPR spectrums, each EPR spectrometer being coupled to one of the first group of flow systems. The at least one processor is generally configured to determine, for each of the first group of flow systems, at least one property of the fluid based on the EPR spectrum associated with the flow system.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects.

DETAILED DESCRIPTION

Figure 1:
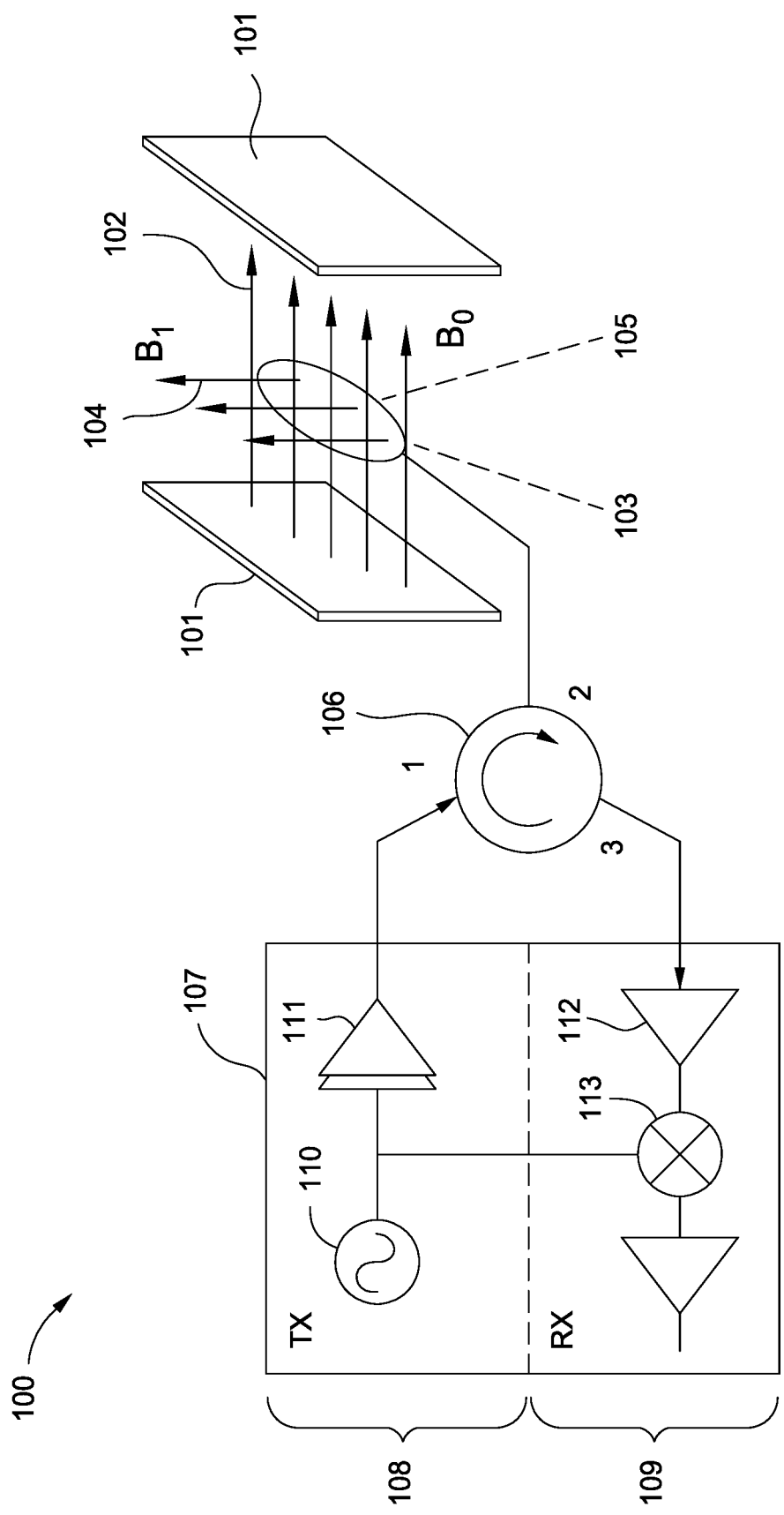
FIG. 1 is a block diagram of an electron paramagnetic resonance (EPR) spectrometer.

Certain aspects of the present disclosure provide methods and apparatus for closed-loop control of a system using one or more electron paramagnetic resonance (EPR) sensors located on-site and properties of a fluid. EPR sensors may be used to measure certain properties associated with any of various suitable species. Furthermore, the properties of these species may be measured by EPR sensors disposed at any of various suitable locations in the production process. With such EPR sensors installed, a change can be applied to the system, the EPR sensors can measure the effect(s) of the change, and then adjustments can be made in real-time. This feedback process may be repeated continuously to control the system.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art at the time of filing the present disclosure.

It is to be understood that both the foregoing general description and the following detailed description are exemplary and explanatory only, and are not restrictive of the invention, as claimed. In this application, the use of the singular includes the plural, the word "a" or "an" means "at least one," and the use of "or" means "and/or," unless specifically stated otherwise. Furthermore, the use of the term "including," as well as other forms, such as "includes" and "included," is not limiting. Also, terms such as "element" or "component" encompass both elements or components comprising one unit and elements or components that comprise more than one unit, unless specifically stated otherwise.

Conventionally, a sample (e.g., of a fluid in a conduit) may be taken from a system and sent off to a laboratory for analysis of certain properties measurable by EPR. Traditional EPR spectrometers have typically been very large and are thus housed in a laboratory, rather than being available on location (e.g., at a production well or injection well). However, this off-site analysis process is too slow to effect a change in the system in real-time based on the sample. Furthermore, the analysis may not be reliable enough or consistent enough.

Accordingly, certain aspects of the present disclosure provide for closed-loop control of the system using an EPR sensor located on-site. With such an EPR sensor, a change can be applied to the system, the EPR sensor can measure the effect(s) of the change, and then adjustments can be made in real-time. This process can be repeated.

FIG. 1 is a block diagram of an example EPR spectrometer 100, in accordance with certain aspects of the present disclosure. The EPR spectrometer 100 may generally use building blocks similar to those of a traditional EPR spectrometer. For example, the EPR spectrometer 100 may include one or more magnets 101, a resonator 103, and a transceiver 107, which includes both transmit (TX) circuitry 108 and receive (RX) circuitry 109 (also referred to as a transmitter and a receiver, respectively).

For certain aspects, the transceiver 107 may be a microwave transceiver, operating at frequencies between 300 MHz and 300 GHz, for example. The TX circuitry 108 may include a frequency synthesizer 110 and a power amplifier 111 coupled between the output of the frequency synthesizer 110 and a circulator 106 (e.g., at port 1 thereof). The TX circuitry 108 is coupled to the resonator 103 via the circulator 106, so that the energy of the source transmission does not overwhelm the sensitive circuits of the RX circuitry 109. The output of the circulator 106 (e.g., at port 2) passes to the resonator 103, which creates a radio frequency (RF) electromagnetic field 104 ($B_1$ field) whose magnetic component is largely perpendicular to that of the static DC magnetic field 102 ($B_0$ field or Zeeman field).

A magnetic field generator provides the static DC magnetic field 102 utilizing magnets 101, coils, or the like. The resonator 103 and sample chamber therein are placed inside the magnets 101 and/or coils that generate the DC magnetic field $B_0$. The sample chamber is designed to allow fluids to flow therethrough. The fluid flow might be that of a full tubular in wellsite equipment or a sidestream to which a subset of the main flow has been directed. In a downhole apparatus, the fluid flow might be that coming from a specific interval of the reservoir, such as directed by a downhole control valve or similar device. The presence of the Zeeman field introduces an energy difference $\Delta E$ between the two spin states of an unpaired electron: parallel and anti-parallel to $B_0$, with $\Delta E$ being proportional to $B_0$. At its resonant frequency, the resonator 103 produces the RF magnetic field $B_1$. Using the notation h for the Planck constant, then at that RF frequency (f) where hf equals $\Delta E$ (i.e., the Larmor frequency), spin transitions between the two up and down spin states occur, resulting in absorption of RF energy in the sample. In a reflection-type resonator, this results in a change in the level of reflected power from the resonator. This reflected power from the resonator is coupled to the receiver via the circulator 106 (e.g., at port 3). For certain aspects, the receiver may include a low noise amplifier (LNA) 112, a mixer 113 coupled to the output of the LNA 112 and the output of the frequency synthesizer 110, and an amplifier 114 coupled to the output of the mixer 113.

As noted by International Patent Application Publication No. 2016187300 to Babakhani et al., entitled "Electron Paramagnetic Resonance (EPR) Systems with Active Cancellation" and filed May 18, 2016, the circulator might not provide complete isolation between the TX and RX circuitry, in which case an active cancellation component may be added to the EPR spectrometer. The entire contents of WO 2016187300 are herein incorporated by reference.

The resonator 103 may be excited with continuous wave or pulsed excitation. In one aspect, the EPR sensor is a sensor that operates at 1 GHz or higher. In other aspects, the EPR sensor may operate at lower frequencies. For certain aspects, the EPR sensor may operate in the range of 3-5 GHz.

It is known that the resonant frequency of a fluid-filled cavity changes depending on the fluid properties therein, as does the efficiency of the coupling of the electromagnetic field to the cavity. The pertinent electrical parameters of the cavity are its dielectric and conductivity properties, which combine into an effective permeability according to the formula $\varepsilon+i\sigma/\omega$, where $\varepsilon$ is the ratio of electrical displacement field to electric field, $\sigma$ is the conductivity, and $e^{-i\omega t}$ is the variation of the field in time (i.e., $\omega$ is the radial frequency, equal to $2\pi f$ where f is excitation frequency). The displacement field can be out of phase with the electric field, in which case $\varepsilon$ can be viewed as a complex number ($\varepsilon'+i\varepsilon''$), or else the imaginary component of $\varepsilon$ can be incorporated into the conductivity. In this text, and as is common in the electromagnetic community, the term "permittivity" is used to refer to both the complex value $\varepsilon+i\sigma/\omega$, and also to just the dielectric component, $\varepsilon$. The intended meaning will be clear to a person having ordinary skill in the art. The term $i\omega\varepsilon''+\sigma$ is commonly called the AC conductivity.

When "considering polar particles in a solvent, the permittivity may be approximated as $\varepsilon=\varepsilon_s+(\varepsilon_c-\varepsilon_s)/(1+(i\omega\tau)^{(1-\alpha)})+i\sigma/\omega$, where $\varepsilon_s$ is solvent permittivity (e.g., hexane), $\varepsilon_c$ is the crude component (e.g., asphaltene), $\alpha$ represents distribution of relaxation times, and $\tau$ is the average relaxation time. Considering this expression, then in low frequency, the DC conductivity component will dominate the AC conductivity, whereas as the frequency increases, then dipole relaxation will dominate as $\varepsilon''$ increases with frequency. This permittivity model was first proposed in Cole, K. S. et al., "Dispersion and Absorption in Dielectrics," *J. Appl. Phys.*, 9, 341-351 (1941).

The magnetic properties of the medium are given by the permeability $\mu$, which is the ratio of magnetic flux intensity B to the magnetic field intensity H. In air, the permeability is denoted $\mu_0$. More generally one can write $\mu=\mu_0(1+\chi)$, where $\chi$ is termed the "susceptibility." The B and H fields may be out of phase, in which case $\mu$ and $\chi$ are also complex numbers. The imaginary component of $\chi$ is called its "AC magnetic susceptibility." A classical interpretation of the EPR signal is that the applied magnetic field induces a change in the AC magnetic susceptibility. Knowledge of $\varepsilon$, $\sigma$, and $\mu$ can be used to identify fluid components; for example, $\varepsilon$ is about 80 in water, 2-5 in oil, and 1 in a gas. $\sigma$ will be virtually zero in hydrocarbons, but nonzero if there is a mix of salty brine water along with the oil. $\mu$ will typically be close to 1, but magnetic particles (e.g., from the wall of iron tubulars or from some minerals) can increase $\mu$.

Figure 2:
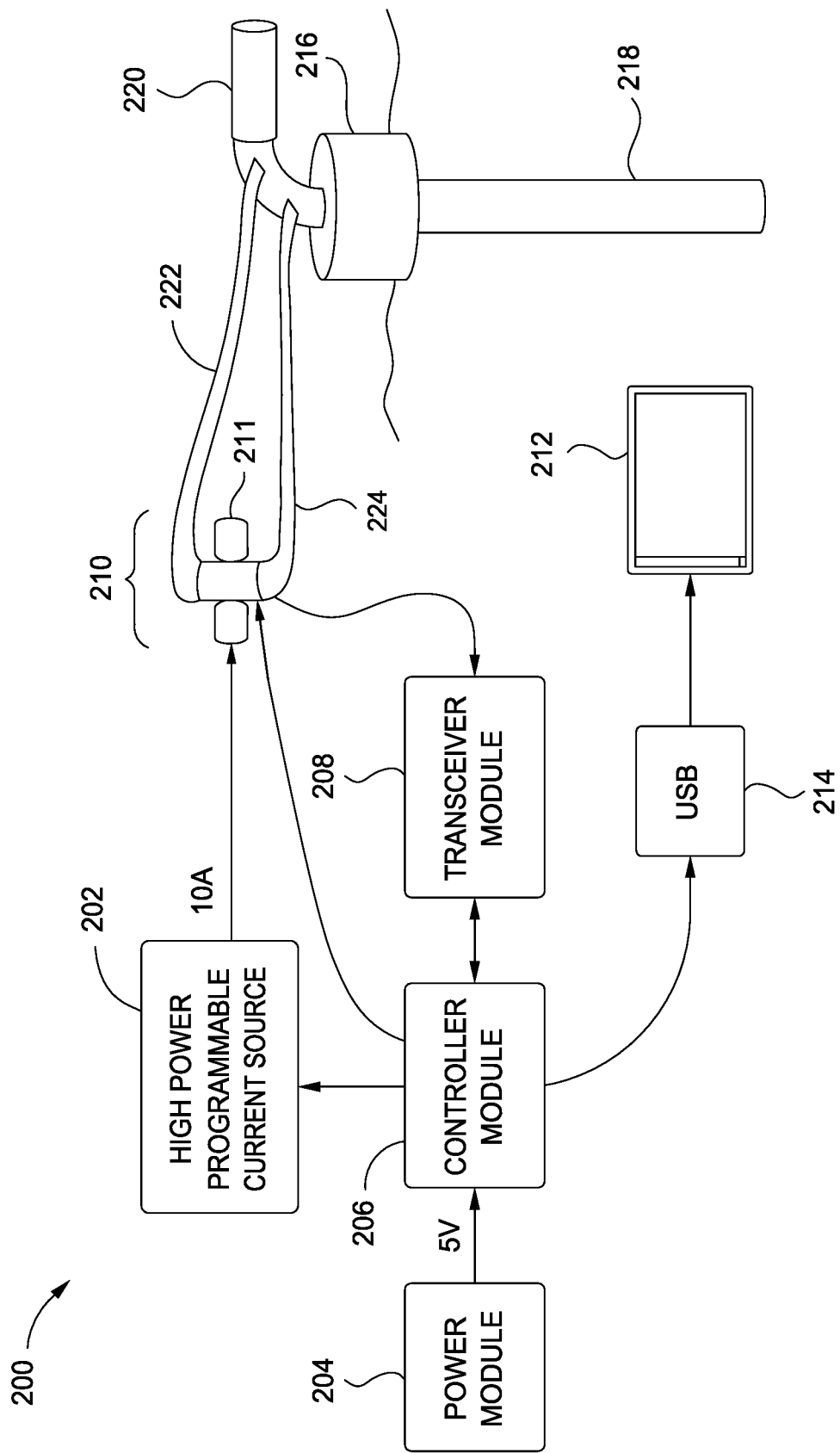
FIG. 2 is a block diagram of an example EPR system that can receive pressurized fluid from a wellbore, in accordance with certain aspects of the present disclosure.

FIG. 2 is a block diagram of an example EPR system 200, in accordance with certain aspects of the present disclosure. As shown, the EPR system 200 comprises five modules: a high power programmable current source 202, a power module 204, a controller module 206, a transceiver module 208, and a resonator assembly 210. The high power programmable current source 202 may be implemented by a power supply with, for example, a gain of 5 A/V capable of 10 A with a 100 mH load. For certain aspects, an appropriate level of accuracy is 0.1% (±0.01 A). The output of this programmable current source 202 feeds a magnet 211 in the resonator assembly 210 to control the magnetic field. The controller module 206 may be capable of outputting a control voltage (e.g., ranging from 0 V to 2 V) to control the high power programmable current source 202. The power module 204 may be a system capable of transforming mains electricity (e.g., 120 VAC at 60 Hz) to one or more DC voltages (e.g., 12 VDC, 5 VDC, and/or 5.5 VDC) for use in the EPR system 200. The transceiver module 208 may be an EPR frequency board, capable of generating an RF signal for a resonator in the resonator assembly 210. Two board options may be considered for the transceiver module: an integrated circuit (IC) transceiver board and a discrete component transceiver board. For example, the discrete component transceiver board may use a 12 VDC power supply voltage output by the power module 204. Alternatively, the IC transceiver board may use a 5 VDC power supply voltage, which may be buffered through the controller module 206.

The EPR system 200 may also include a human-machine interface (HMI) 212, such as a computer or any of various other devices (e.g., a tablet, a smartphone, and the like) with a suitable processing system, a display, and means for inputting instructions (e.g., a keyboard, mouse, stylus, touchscreen, and the like). The HMI 212 is capable of sending commands to and receiving data from the controller module 206 (e.g., via a USB/UART bridge 214 or via wireless communications, such as WiFi according to IEEE 802.11).

As shown in FIG. 2, the EPR system 200 may remain in continuous fluid communication with equipment at a wellsite, such as a wellhead 216 disposed at the surface and/or production tubing 218 disposed in a wellbore. The production tubing 218 may be one of multiple tubulars in the wellbore. It is not uncommon, for example, that the production tubing 218 is contained within a number of strings of casing (not shown). The wellhead 216 as drawn figuratively represents the connection between a surface production pipeline 220 and the production tubing 218. As is well known in the industry, wellheads typically have a number of sample ports thereon, which allows an operator access to the fluid flowing from a reservoir. During production, the flow path from the production tubing 218 through the wellhead 216 to the pipeline 220 is generally maintained as a pressure barrier to prevent reservoir fluids from polluting the air and ground nearby. Consequentially, the fluid communication channels 222, 224 from the wellhead 216 to the resonator assembly 210 and back should be able to withstand internal fluid pressure. The connections of the channels 222, 224 to the wellhead 216 may be permanently welded or may be hose connections that are certified for exposure to oilfield fluids and pressures.

As drawn, the fluid connection for the channels 222, 224 is made downstream of the wellhead 216 and upstream of the pipeline 220, but other configurations may be utilized, which will be clear to those skilled in the art. For example, the connections may be located further downstream, such as in the vicinity of a pipeline manifold or at sample points along a pipeline as the pipeline transfers fluid from the wellbore to a refinery or vessel. Alternatively, the connections may be below the wellhead 216, such as in a scenario where the resonator assembly 210 is incorporated as an in-well sensor.

Figure 3:
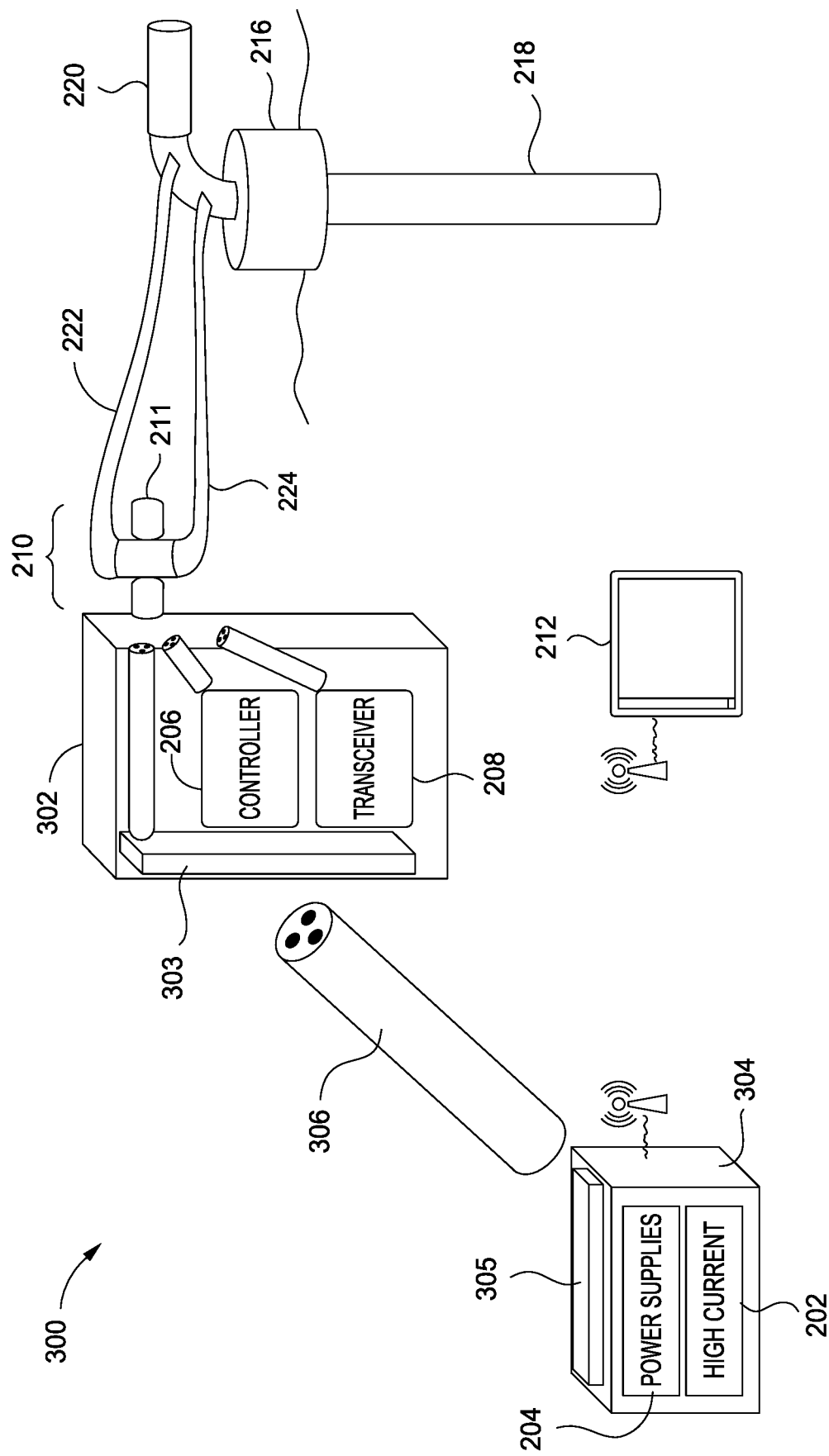
FIG. 3 is a block diagram of an example EPR system in which some components are positioned near the wellbore, whereas other components are located remote from the wellbore, in accordance with certain aspects of the present disclosure.

As illustrated in FIG. 3, the HMI 212 may be some significant distance away from the wellhead 216. In this case, the HMI 212 may be in communication with a portion of the wellsite equipment by means of the cloud and/or other communications network (e.g., WiFi according to the IEEE 802.11 standard). Indeed, in a typical oilfield setting, some components may be positioned close to the wellbore, while others may need to be located relatively far away. RF components, such as the resonator assembly 210 and the transceiver module 208, should be typically spaced within a few feet of each other. To keep the channels 222, 224 short, the resonator assembly 210 may most likely also be positioned within a few feet of the wellhead 216. This means that these RF components may most likely be enclosed in one or more explosion-proof housings 302 to avoid any safety issues, should there be accidental release of hydrocarbon at the wellhead 216. The power supplies (e.g., the high power programmable current source 202 and the power module 204), audio-frequency devices, etc. can be some distance removed from the wellhead without issue, so these components need not be in explosion-proof housing(s), but might benefit from being in housings 304 to provide insulation from the rain, snow, heat, etc. The proximate components (e.g., in the housing(s) 302) may include one or more junction boxes 303. Similarly, the remote components (e.g., in the housing(s) 304) may include one or more junction boxes 305 for coupling to the junction boxes 303 via a cable 306. For certain aspects, the cable 306 may be a multicore armored cable.

Figure 4:
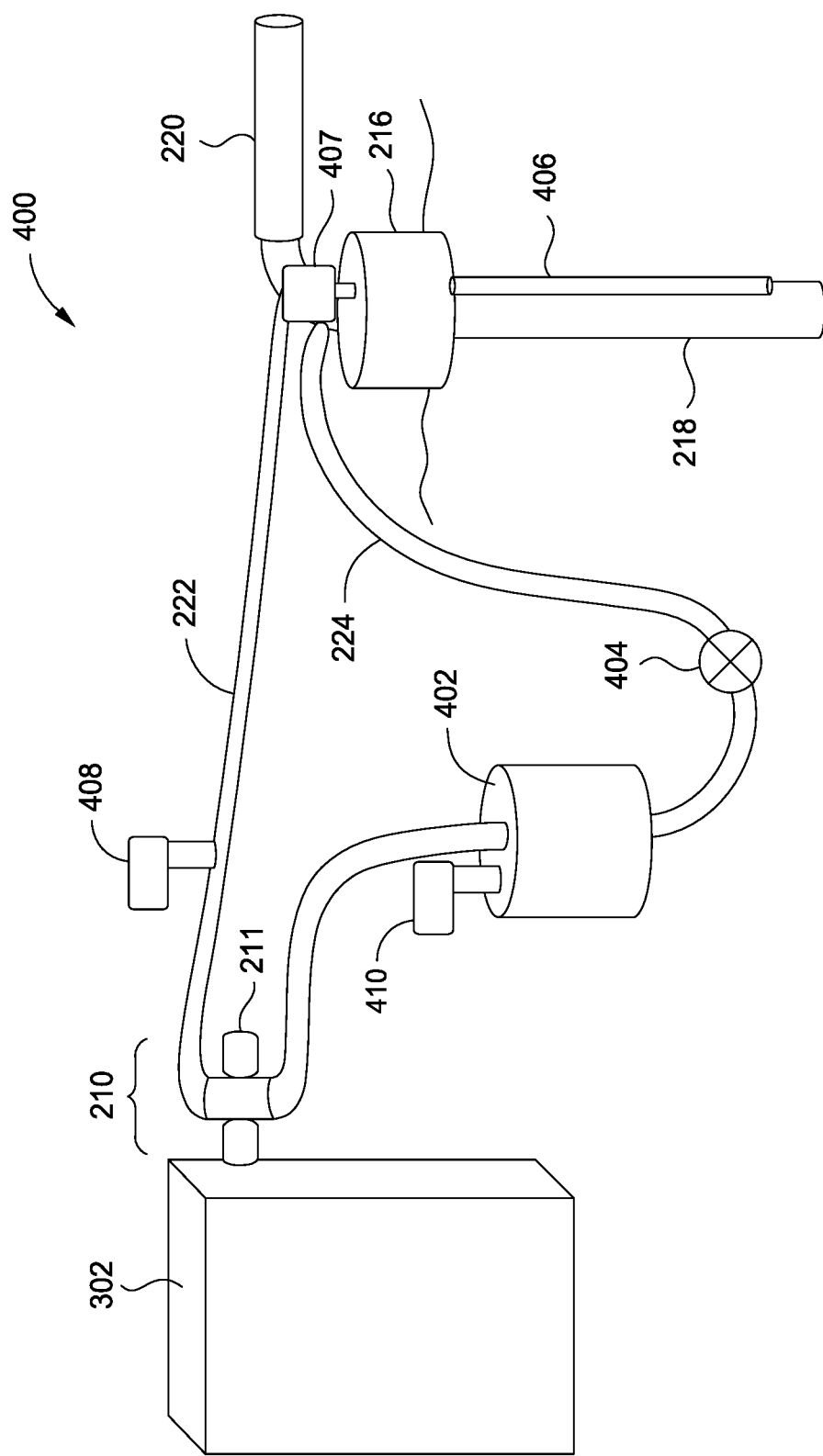
FIG. 4 is a block diagram of an example EPR system with a separator and a pump to increase the sensitivity of an EPR spectrometer to a particular component of a multiphase fluid from a wellbore, in accordance with certain aspects of the present disclosure.

FIG. 4 is a block diagram of an example EPR system 400 with a separator 402 and a pump 404 to increase the sensitivity of an EPR spectrometer to a particular component of a multiphase fluid from a wellbore, in accordance with certain aspects of the present disclosure. The separator 402 may be used to partially separate multiple phases from the multiphase fluid received from the wellhead 216 via the fluid communication channel 224. For example, the opening and closing of one or more valves in or associated with the separator 402 may be controlled to temporarily store the multiphase fluid in the separator, allow time for the separator to separate at least a portion of one phase from one or more other phases in the multiphase fluid, and permit the resulting fluid to enter the resonator assembly 210 for performing EPR spectroscopy. For example, the separator 402 may receive a multiphase fluid that is 98% water and 2% oil and generate a fluid that is 20% oil and 80% water. In this manner, the multiphase fluid reaching the resonator cavity have a higher percentage of oil, such that the paramagnetic species of interest in the oil (e.g., asphaltene) will have a higher concentration, thereby resulting in an EPR spectrometer with increased sensitivity.

For certain aspects, the separated portion of the one phase may be removed from the separator 402 by the optional fluid access 410. The pump 404 may be used to pump the multiphase fluid from the wellhead 216 into the separator 402 via the fluid communication channel 224. The pressure and/or temperature of the resulting fluid in the fluid communication channel 222 may be measured by one or more gauges 408.

For certain aspects, an injection line 406 may be disposed in the wellbore (e.g., a production well), which may run adjacent to the production tubing 218. For other aspects, the injection line 406 may be disposed in a different wellbore (e.g., an injection well). A fluid (e.g., a gas, such as carbon dioxide ($CO_2$), or an inhibitor) may be injected into the injection line 406 via an injection valve 407, which may be located at the wellhead 216.

For certain aspects, the separator 402 may operate based on gravity and the natural separation of an unstable emulsion (e.g., of oil and water) or other colloid that occurs over time. For other aspects, the separator 402 may break the emulsion through the addition of a chemical component. In this case, the chemical component may be added, for example, via the injection valve 407 or another port at the wellhead 216. In the case of a multiphase fluid (e.g., a colloid) with a gas phase, the gas may be vented out (e.g., via the fluid access 403 or another port) before the remaining fluid is allowed to proceed to the resonator assembly 210 (e.g., by controlling the valves in the separator).

Figure 5:
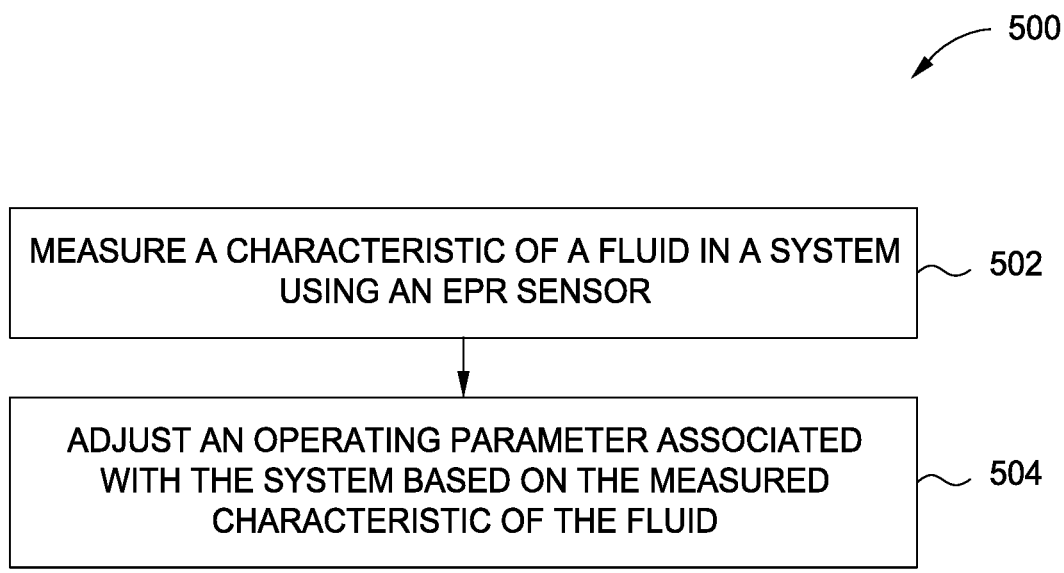
FIG. 5 is a flow diagram of example operations for controlling a system based on EPR sensing, in accordance with certain aspects of the present disclosure.

FIG. 5 is a flow diagram of example operations 500 for controlling a system based on EPR sensing, in accordance with certain aspects of the present disclosure. The operations 500 may begin, at block 502, by measuring a characteristic of a fluid in a system using an EPR sensor. At block 504, an operating parameter associated with the system is adjusted based on the measured characteristic of the fluid. The operations 500 may be repeated to effect closed-loop control of the system using the EPR sensor.

Any of various species in the fluid may be measured by the EPR sensor. For example, the species being sensed may include free radical and transition metal ions, such as asphaltene (free radicals), scales, iron oxides, iron carbonates, iron sulfides, and tracers that have an EPR signature.

The EPR sensor may provide a spectroscopic view of the paramagnetic components of the sample, but may also have additional sensors thereon. For example, the EPR sensor may derive permittivity, conductivity, density, viscosity, pressure, and/or temperature. In the case of permittivity, the EPR sensor may derive a spectrum of complex permittivity values over a frequency range.

The EPR sensor may be disposed at any of various suitable locations (e.g., to implement the operations 500). For example, the EPR may be located downhole, at a wellhead producer (i.e., the wellhead of a production well), at a wellhead injector (i.e., the wellhead of an injection well), at a header or gathering facility, at a test separator or other separator, adjacent to a pipeline, at a processing facility, at a storage, at an input to a refinery, or in the refinery process.

In this manner, the species of interest may be continuously monitored throughout a field or a process, at one or more locations as desired. Furthermore, the system can be adjusted in real-time based on the characteristics of the species measured with the EPR sensor(s).

For example, the EPR sensor may be positioned at a wellhead (e.g., of an injection well or a production well) to measure asphaltenes. Chemicals may be injected into the well, and oil with asphaltenes therein may rise to the surface. The EPR sensor will allow for measurements of the resulting asphaltenes, so the amount of chemicals being injected can be adjusted accordingly. For example, if an insufficient amount of a particular chemical is being injected, the EPR sensor may measure a decrease in surface asphaltenes in real-time, and the chemical injection may be increased based on these measurements. Alternatively, if excessive chemicals are being injected, the operator and/or the EPR system can decrease those chemicals, for example, until a decrease in asphaltene is sensed, which may thereby identify an optical amount of chemicals. With this closed-loop control, an optimal amount of chemicals may be injected, which should save money. In other words, certain aspects of the present disclosure provide an online monitoring EPR sensor (e.g., at the wellhead) that generates a signal to optimize, or at least adjust, chemical injection.

Example Sensing of a Multiphase Fluid Using EPR

Knowing component percentage in a complete multiphase fluid may not be sufficient to guide subsequent decision making at the well (e.g., a decision to change chemical injection parameters, type of chemical, etc.) because the appropriate measurement may be the percentage in the oil phase, not the percentage in the combined multiphase flow. For example, consider that a certain crude oil has 5% asphaltene as it exits the sandface of the reservoir and then commingles with water as it returns to the surface, such that a surface measurement gives 90% water and 10% oil, where 5% of that oil is asphaltene (i.e., 0.5% of the total fluid). Now consider that chemical instability or pressure drop causes most of the asphaltene to drop out of the oil, so that at surface a meter will read 90% water and 10% oil, where 1% of the oil is asphaltene. In this scenario, a correct response might be to increase injection of solvent into the well, or to get ready for an intervention with a coiled-tubing unit to unclog the well, because the bulk of the asphaltene has not made it to the surface. For a different scenario, suppose that the water cut increases with no increase in drop-out, so that the surface meter reads 98% water and 2% oil, where 5% of that oil is asphaltene. In this scenario, a correct response might be to reduce the amount of solvent. Both scenarios give 0.1% asphaltene ratio. If the only measurement available was coming from EPR sensing of the total fluid, then it may be quite difficult to make a guided decision. None of the references cited herein anticipate using spectrometry to extract the EPR signal of a single component of a multiphase fluid. This ability may be even more useful when employing the EPR signal to drive a control system or feedback loop, as described herein.

Figure 6:
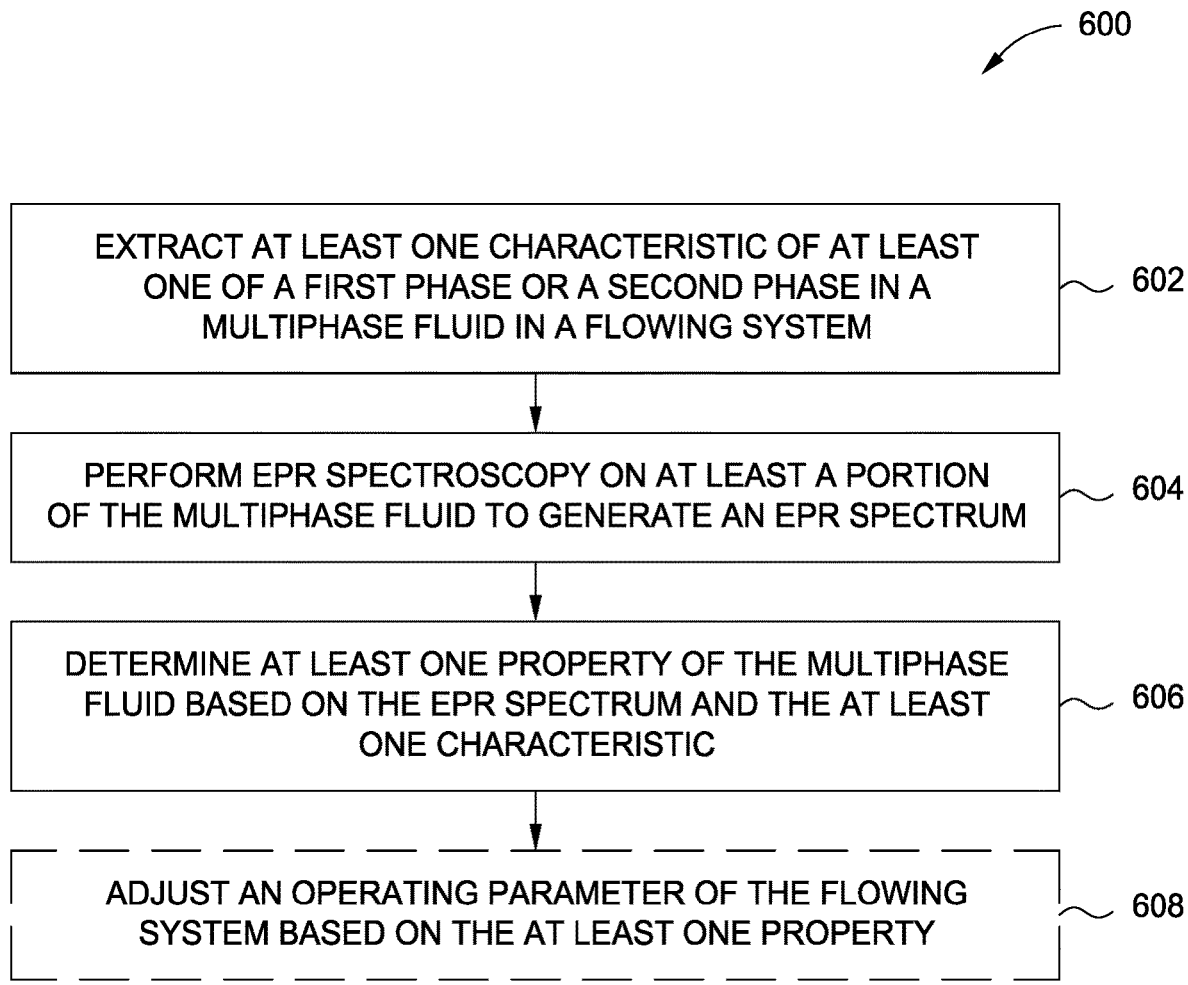
FIG. 6 is a flow diagram of example operations for sensing a multiphase fluid using EPR, in accordance with certain aspects of the present disclosure.

FIG. 6 is a flow diagram of example operations 600 for sensing a multiphase fluid, in accordance with certain aspects of the present disclosure. The operations 600 may be performed by an EPR system, for example.

The operations 600 may begin, at block 602, by extracting at least one characteristic of at least one of a first phase or a second phase in the multiphase fluid in a flowing system. At block 604, EPR spectroscopy may be performed (e.g., using an EPR spectrometer) on at least a portion of the multiphase fluid to generate an EPR spectrum. At block 606, the system may determine at least one property of the multiphase fluid based on the EPR spectrum and the at least one characteristic.

According to certain aspects, the operations 600 may further involve adjusting an operating parameter of the flowing system based on the at least one property at optional block 608. For certain aspects, the operations 600 may further entail repeating the extracting at block 602, the performing at block 604, the determining at block 606, and the adjusting at optional block 608 for automated closed-loop control of the operating parameter. These blocks may be repeated one or more times. The operating parameter may include a rate or a volume of fluid injection into the flowing system. Additionally or alternatively, the operating parameter may include a pressure, a type, or a concentration of an injected fluid introduced into the flowing system.

According to certain aspects, the flowing system comprises a system for hydrocarbon recovery operations. In this case, the first phase may be an oil component of the multiphase fluid, and the second phase may be a water component or a gas component of the multiphase fluid. For certain aspects, the system for hydrocarbon recovery operations includes a wellhead. In this case, the performing at block 604 may involve performing the EPR spectroscopy on the at least the portion of the multiphase fluid at or adjacent the wellhead. For certain aspects, the at least one characteristic includes a volume fraction of the oil component. In this case, the at least one property may include a concentration of asphaltene in the oil component (as opposed to a concentration of asphaltene in the multiphase fluid).

According to certain aspects, the operations 600 may further entail separating at least a portion of the second phase from the multiphase fluid (e.g., 95% water and 5% oil) to leave a remaining fluid (e.g., now 80% water and 20% oil). For certain aspects, the at least the portion of the multiphase fluid includes the remaining fluid, and in this case, the determining at block 606 may involve determining at least one property of the remaining fluid.

According to certain aspects, the operations 600 may further include controlling one or more valves to at least one of: (1) store the multiphase fluid in a separator, (2) separate at least a portion of the second phase from the multiphase fluid, or (3) allow the at least the portion of the multiphase fluid to enter a resonator from the separator for performing the EPR spectroscopy at block 604.

According to certain aspects, the operations 600 may further involve determining at least one electromagnetic attribute of the at least the portion of the multiphase fluid. In this case, determining the at least one property of the multiphase fluid at block 606 may entail determining the at least one property of the multiphase fluid based on the EPR spectrum, the at least one characteristic, and the at least one electromagnetic attribute. For certain aspects, determining the at least one electromagnetic attribute is based on performing the EPR spectroscopy at block 604. In this case, the at least one electromagnetic attribute includes at least one of a conductivity, a dielectric property, a magnetic susceptibility, or a magnetic permeability, of the at least the portion of the multiphase fluid.

According to certain aspects, the operations 600 may further include adjusting an operating parameter of the flowing system based on a deviation of a current value of the at least one property from a baseline value of the at least one property. For certain aspects, the baseline value was generated by: (1) repeating the extracting at block 602, the performing at block 604, and the determining at block 606 over time to generate multiple values of the at least one property; and (2) deriving the baseline value based on the multiple values of the at least one property. For certain aspects, the operations 600 may further involve: (1) repeating, after the adjusting, the performing the EPR spectroscopy at block 604 to generate an updated EPR spectrum; and (2) identifying a change in the updated EPR spectrum from a previously generated EPR spectrum.

According to certain aspects, at least one property includes a concentration of asphaltene in the multiphase fluid.

According to certain aspects, the at least one characteristic includes at least one of a volume fraction of the first phase or a volume fraction of the second phase.

Figure 7:
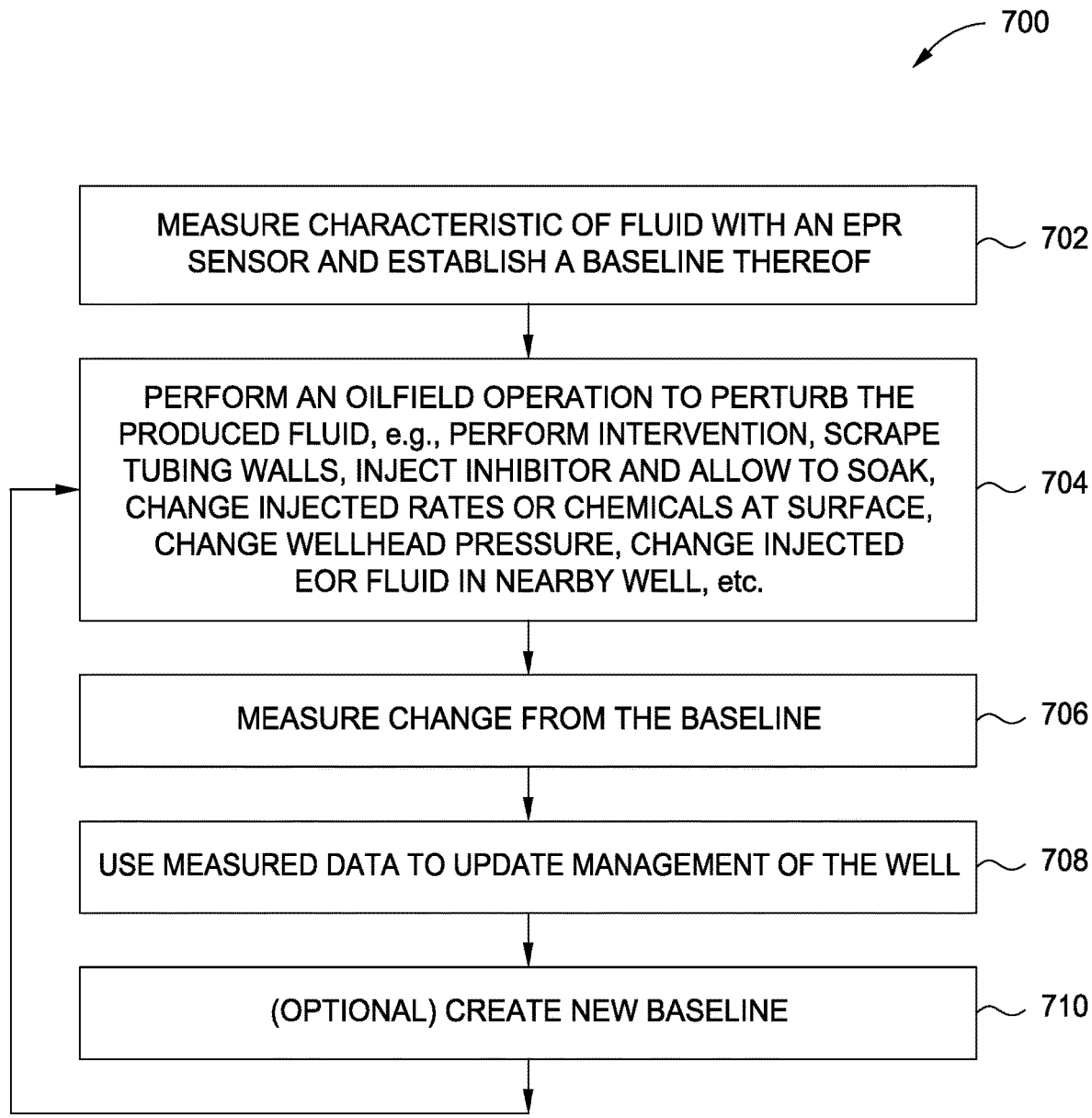
FIG. 7 is a flow diagram of example operations for controlling a system based on EPR sensing, in accordance with certain aspects of the present disclosure.

FIG. 7 is a flow diagram of example operations 700 for controlling a system based on EPR sensing, in accordance with certain aspects of the present disclosure. The operations 700 may be performed by an EPR system, for example.

The operations 700 may begin, at block 702, by measuring a characteristic of a fluid with an EPR sensor (e.g., an EPR spectrometer). For example, the characteristic(s) may include asphaltene parameters, such as concentration, particle size, and/or behavior. For certain aspects, a baseline thereof may also be established at block 702 or prior thereto.

At block 704, an oilfield operation may be performed to perturb a produced fluid. Example oilfield operations may include, but are not limited to, performing an intervention, scraping tubing walls, injecting inhibitor and allowing the inhibitor to soak, changing injection rates or injected chemicals (e.g., at the surface), changing wellhead pressure, changing injected enhanced oilfield recovery (EOR) fluid (e.g., in a nearby well), and the like.

At block 706, a change from the baseline may be measured. For certain aspects, the EPR sensor may be used to measure additional data, and a change in the data may be determined. For example, the change from the baseline may include a change in concentration, volatility, spectrum, and/or other behaviors.

At block 708, the measured data may be used to update management of the well (e.g., by adjusting an operating parameter). For example, a treatment change may be initiated, which may include, for example, a change in the level of inhibitor(s) and/or other chemical(s) injected, a change in the type or concentration of the injected fluid, a change in the operational condition (e.g., change pressure, temperature, or other parameter), or a change in an injection parameter (e.g., rate). More specifically, the system may be tuned by increasing or reducing the volume or rate of a chemical inhibitor, not only ascertaining the right amount (or rate) of a chemical for the condition, but also tuning per other (changing) operational conditions. Furthermore, the system may be tuned by (continuously) adjusting one or more operational conditions. For example, by increasing pressure in the system, an operator may be able to keep asphaltenes from coming out of solution, which may eliminate the use of chemicals in some scenarios. For certain aspects, a new baseline may be created at block 710. Then, the operations 700 may be repeated, starting with block 704 as illustrated in FIG. 7. The ability to continuously measure in real-time allows an operator to try various adjustments to the system, analyze the effects, and try something different (e.g., different types of inhibitors and/or different types of operation modes).

Quality and (Flow) Monitoring of Sales Oil

In the case of a pipeline as an example conduit, one or more EPR sensors may be used for inspection and quality control of the pipeline. A fluid supplier (e.g., an oil or gas company) may claim that the fluid being supplied has a particular composition. The pipeline company may want to monitor that the actual fluid being supplied matches the composition claims made by the fluid supplier and look for changes. If the composition of the fluid does not match what has been claimed, the pipeline company can ask the fluid supplier to make adjustments.

Figure 8:
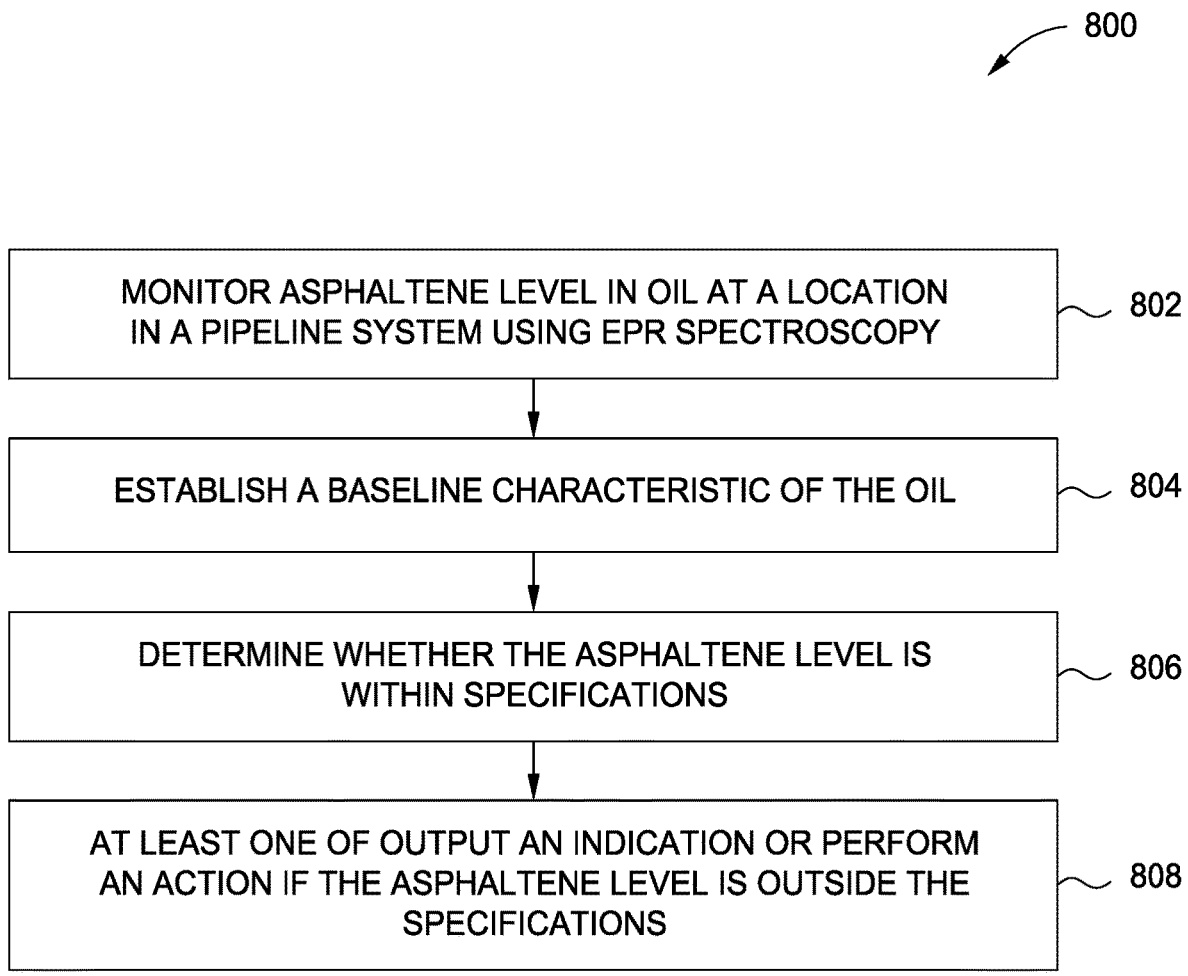
FIG. 8 is a flow diagram of example operations for monitoring oil in a pipeline system using EPR, in accordance with certain aspects of the present disclosure.

FIG. 8 is a flow diagram of example operations 800 for monitoring oil in a pipeline system using EPR, in accordance with certain aspects of the present disclosure. The operations 800 may begin, at block 802, by monitoring the asphaltene level in the oil at a location in the pipeline system using EPR spectroscopy. For example, the location may be at the point of entry into the pipeline system or along the length of the pipeline system. For certain aspects, a baseline characteristic of the oil may be established at optional block 804. In this case, this oil's baseline may be compared with those of other fluids (e.g., oils) entering the same pipeline system, if the fluids are commingled. At block 806, the system may determine whether the asphaltene level is within specifications. For certain aspects, the system may report the results. If the asphaltene level is determined to be outside the specifications at block 806, then at block 808, the system may output an indication and/or perform an action to bring the asphaltene level within the specifications. This determination may be performed concurrently with a determination of other parameters of the crude oil, such as pH, level of sulfur, etc.

Field-Wide Monitoring of Asphaltene Using EPR

According to certain aspects, field-wide monitoring of asphaltenes may be performed using EPR sensors. Using EPR sensors in this manner, there may be an observed, distinct difference in asphaltenes between carbon dioxide ($CO_2$) flood areas and water ($H_2O$) flood areas. Areas exposed to $CO_2$ over time may have more deposited asphaltenes than areas less exposed to $CO_2$. Therefore, asphaltene measurement may be used as a tool to determine injection patterns for enhanced oil recovery (EOR). In this manner, the effects of $CO_2$ injection (e.g., where the $CO_2$ is going) may be determined based on changes in asphaltene concentration as measured by the EPR sensors (e.g., at the wellheads).

For certain aspects, a survey of the wells in the field may be performed, prior to $CO_2$ injection (e.g., to establish a baseline). Then, asphaltene concentrations may be monitored over time on different producers. Based on the asphaltene concentrations, operating parameters for one or more of the wells may be adjusted. For example, the injection pattern of $CO_2$ may be changed, or certain chemicals (e.g., polymers) may be added in an effort to influence how $CO_2$ moves within the reservoir.

Figure 9:
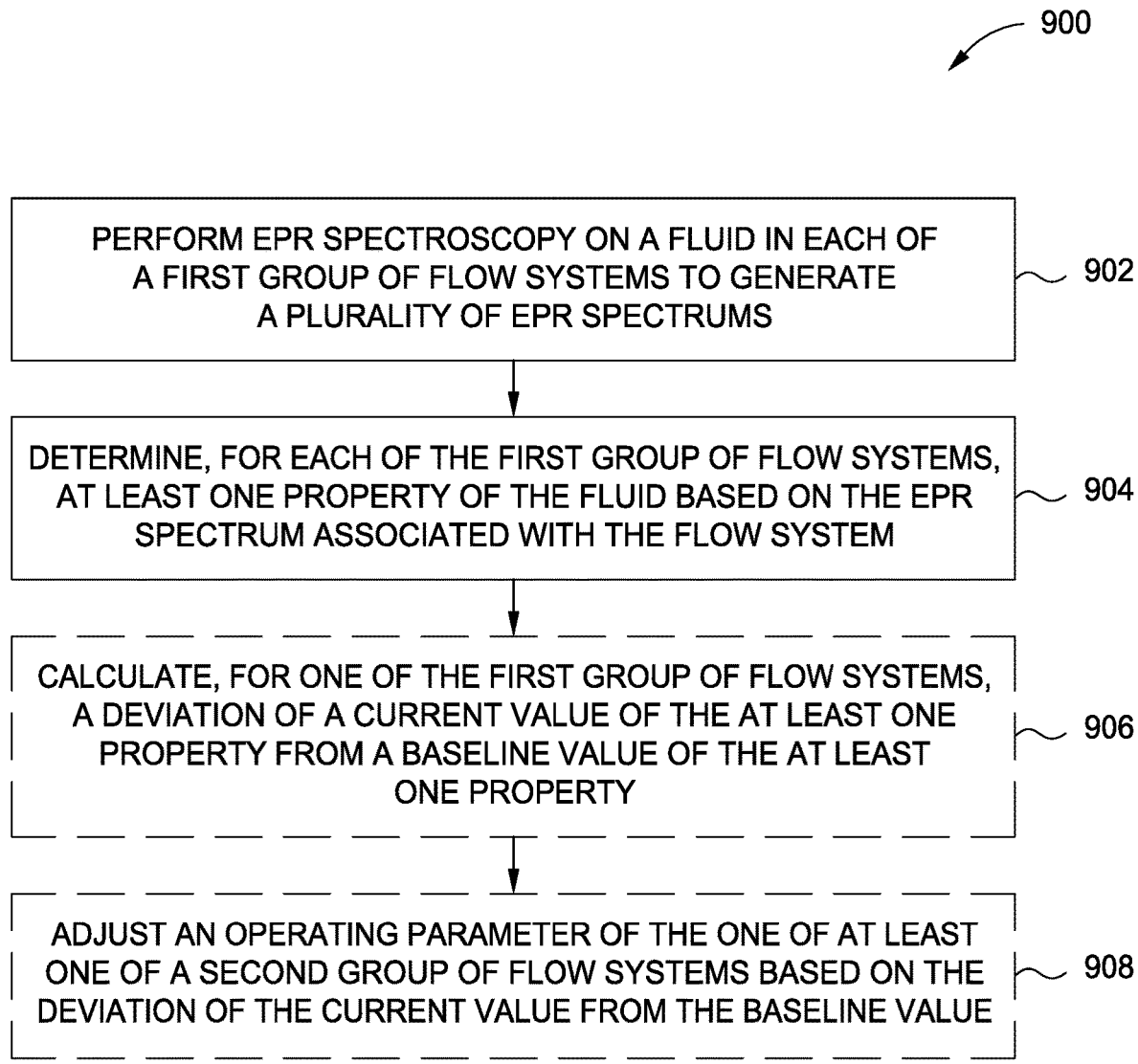
FIG. 9 is a flow diagram of example operations for monitoring multiple flow systems using EPR, in accordance with certain aspects of the present disclosure.

FIG. 9 is a flow diagram of example operations 900 for monitoring multiple flow systems using EPR, in accordance with certain aspects of the present disclosure. The operations 900 may begin, at block 902, by performing EPR spectroscopy on a fluid in each of a first group of flow systems to generate a plurality of EPR spectrums. For each of the first group of flow systems, at block 904, at least one property of the fluid may be determined based on the EPR spectrum associated with the flow system.

According to certain aspects, the operations 900 may further involve calculating, for one of the first group of flow systems at optional block 906, a deviation of a current value of the at least one property from a baseline value of the at least one property. For certain aspects, the baseline value of the at least one property is based on a plurality of historic values of the at least one property for the first group of flow systems. For certain aspects, the baseline value was generated by: (1) repeating the performing at block 902 and the determining at block 904 over time to generate multiple values of the at least one property for each of the first group of flow systems; and (2) deriving the baseline value based on the multiple values of the at least one property for each of the first group of flow systems. For certain aspects, the operations 900 may further entail adjusting an operating parameter of at least one of a second group of flow systems, at optional block 908, based on the deviation of the current value of the at least one property from the baseline value of the at least one property. The second group of flow systems may be different from the first group of flow systems. For certain aspects, the operating parameter includes a rate or a volume of fluid injection into the at least one of the second group of flow systems. Additionally or alternatively, the operating parameter includes a pressure, a type, or a concentration of an injected fluid introduced into the at least one of the second group of flow systems. For certain aspects, the multiple flow systems comprise multiple systems for hydrocarbon recovery operations in a field. In this case, the first group of flow systems may include multiple production wells in the field, and the second group of flow systems may include multiple injection wells in the field.

According to certain aspects, the operations 900 may further involve repeating the performing at block 902 and the determining at block 904 over time to generate multiple values of the at least one property for at least one of the first group of flow systems. In this case, the operations 900 may also include correlating the multiple values of the at least one property for the at least one of the first group of flow systems with other data for the at least one of the first group of flow systems. For certain aspects, the other data includes at least one of production history data, seismic data, or geology data for the at least one of the first group of flow systems. For certain aspects, the operations 900 may further entail adjusting an operating parameter of at least one of a second group of flow systems based on the correlation. The second group of flow systems may be different from the first group of flow systems.

According to certain aspects, the multiple flow systems comprise multiple systems for hydrocarbon recovery operations in a field. In this case, the first group of flow systems includes multiple production wells in the field. For certain aspects, the fluid in each of the first group of flow systems comprises oil. In this case, the at least one property may include a concentration of asphaltene in the fluid or a concentration of asphaltene in the oil.

According to certain aspects, the operations 900 may further entail determining, for one of the first group of flow systems, at least one electromagnetic attribute of the fluid. In this case, determining the at least one property of the fluid at block 902 involves determining the at least one property of the fluid based on the EPR spectrum and the at least one electromagnetic attribute. For certain aspects, determining the at least one electromagnetic attribute is based on performing the EPR spectroscopy. In this case, the at least one electromagnetic attribute may include at least one of a conductivity, a dielectric property, a magnetic susceptibility, or a magnetic permeability, of the fluid in the one of the first group of flow systems.

According to certain aspects, the fluid in each of the first group of flow systems comprises a multiphase fluid.

According to certain aspects, the operations 900 may further involve adjusting an operating parameter of one of a second group of flow systems. In this case, the multiple flow systems may include multiple systems for hydrocarbon recovery operations in a field, the first group of flow systems may include multiple production wells in the field, and the second group of flow systems may include multiple injection wells in the field. For certain aspects, the operations 900 may further entail, after the adjusting, performing EPR spectroscopy on the fluid in each of the first group of flow systems to generate a plurality of updated EPR spectrums; determining, for each of the first group of flow systems, the at least one property of the fluid based on the updated EPR spectrum associated with the flow system; comparing the plurality of updated EPR spectrums with the previously generated plurality of EPR spectrums; and determining reservoir continuity in the field based on the comparison.

Figure 10:
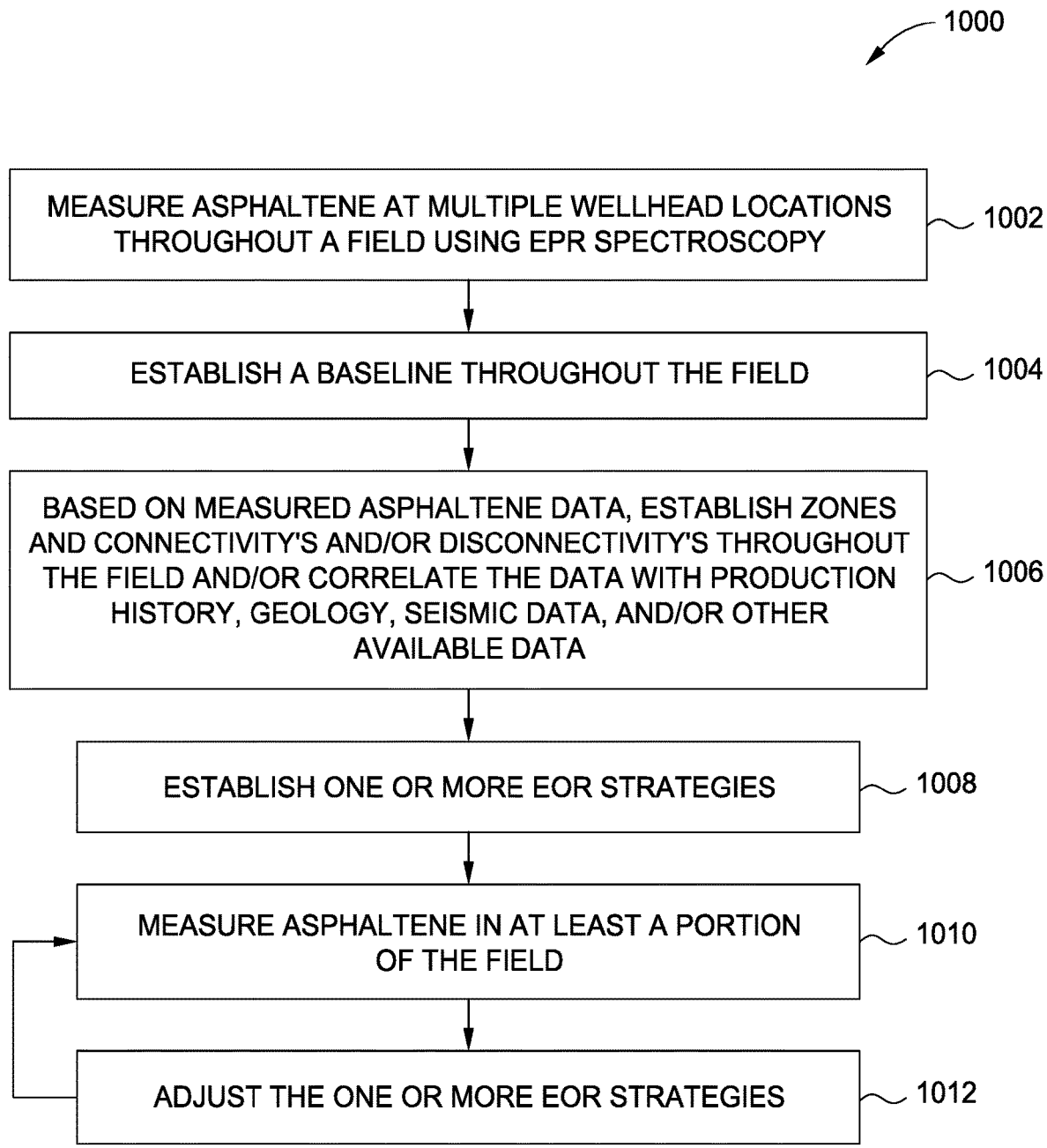
FIG. 10 is a flow diagram of example operations for field-wide monitoring using EPR, in accordance with certain aspects of the present disclosure.

As a specific example, FIG. 10 is a flow diagram of example operations 1000 for field-wide monitoring of asphaltene using EPR, in accordance with certain aspects of the present disclosure. The operations 1000 may begin, at block 1002, by measuring asphaltene at multiple wellhead locations throughout a field using EPR spectroscopy. The asphaltene may be measured at the surface or subsurface at the wellhead locations. These measurements may be more relevant in more mature fields with some form of EOR operation starting or ongoing (e.g., using secondary or tertiary methods).

At block 1004, a baseline may be established throughout the field. Depending on the nature of the field, the baseline may take a few different forms. In a new field, the baseline may represent a starting point, whereas in an older field, the baseline may represent a point moving forward.

At block 1006, based on the measured asphaltene data, zones and connectivities (and/or disconnectivities) may be established throughout the field. For certain aspects, this data may be correlated with other data, such as production history, geology, seismic data, and/or other available data.

At block 1008, one or more EOR strategies may be established, based on the information determined at block 1006. For example, these strategies may include fluid injection (e.g., of water or gas) or applying pumping/extraction pressures.

At block 1010, asphaltene may be measured in at least a portion of the field (e.g., partially or fully throughout the field at surface or subsurface). At block 1012, the one or more EOR strategies may be adjusted, based on the measured asphaltene. For certain aspects, blocks 1010 and 1012 may be repeated as desired.

For example, an amount of injected $CO_2$ may be increased (e.g., at block 1012) in a certain injection well (e.g., #5 well). In response, the asphaltene concentration at a particular well (e.g., #2 production well) drops, indicative of asphaltene deposition (e.g., as measured at block 1010). Therefore, the EOR strategy may be adjusted (e.g., at block 1012) to decrease the amount of $CO_2$ injected and/or inject water instead (e.g., into #5 well). This may be done until the asphaltene concentration in the particular well (#2) begins to rise.

As another example, the operations 1000 may be used to map $CO_2$ distribution within a reservoir. For example, an operator may suspect an area with significantly lowered asphaltene at the well has had significantly more exposure to $CO_2$, either over time or by volume (more breakthrough).

Monitoring asphaltenes can be used to map $CO_2$ EOR floods (and potentially water floods). For $CO_2$ flood, the asphaltene content may be measured (e.g., at block 1002) before the addition of $CO_2$. After a $CO_2$ flood is applied, an EPR system may be used to measure the change of the asphaltene content at each well (e.g., at block 1010), which represents the relative amount of $CO_2$ reaching each well. This method shows the $CO_2$ connectivity between wells and can be used to optimize, or at least adjust, the $CO_2$ injection pattern (e.g., at block 1012).

More specifically, in some scenarios, there may multiple production and injections wells in a field, where EPR sensors may be implemented at a portion of these wells. Increasing the $CO_2$ injection in one injection well (e.g., #5 well) may cause the asphaltene content as measured by the EPR sensors to drop in a group of production wells (e.g., #2, #11, and #13 wells), but not change the asphaltene content in any of the other wells in the field. This may lead to the inference that the reservoir intersected by the injection well has good connectivity to reservoir intersected by the particular group of production wells, but not to other wells. Based on such inferences, reservoir continuity may be determined.

In the case of an injector, an injection fluid (e.g., carbon dioxide ($CO_2$) or water) may be injected into an injection well via the injector. This injection fluid may show up in the production fluid being produced from the production well and may be separated out by a separator, for re-use in the injection well. However, the injection fluid coming out of the production well may have some species of interest (e.g., asphaltenes (in gas or solid phase)) that may be undesirable (e.g., because this species can cause problems in the injection well. Therefore, the injection fluid coming out of the production well or out of the separator may be filtered, and an EPR sensor may be used to monitor the injection fluid (e.g., at the wellhead injector).

Asphaltene PVT Measurement and Monitoring Using EPR

Figure 11A:
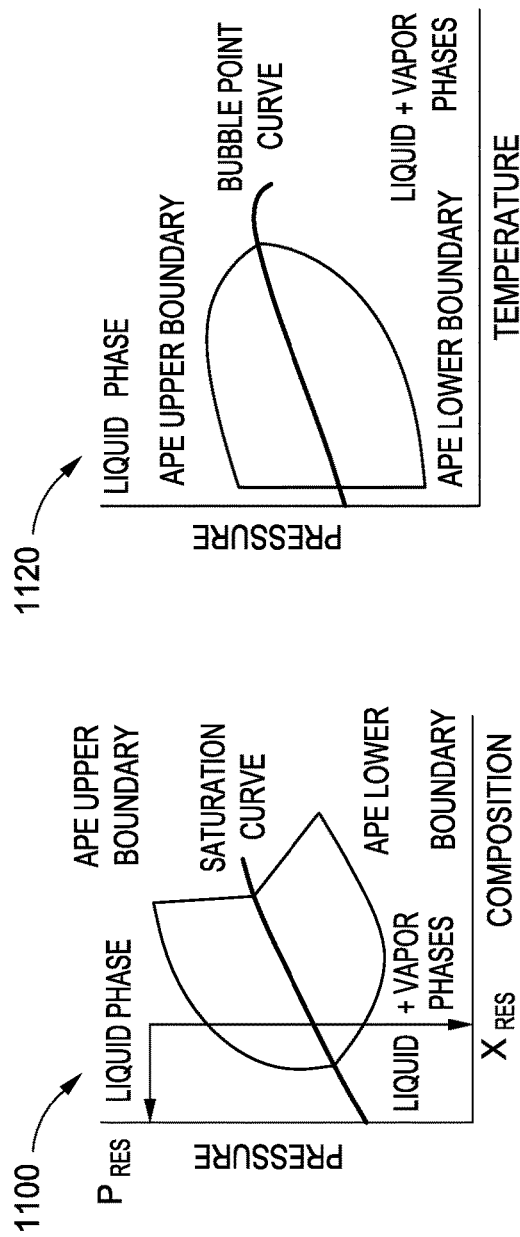
FIG. 11A illustrates different asphaltene phases based on pressure, composition, and temperature, in accordance with the prior art.

According to certain aspects, compositional data from a subject field may be used to establish the asphaltene boundaries for core EOR conditions (e.g., injected water or gas). The asphaltene boundaries (e.g., upper and lower boundaries) may be based on a pressure/volume/temperature (PVT) chart, such as PVT charts 1100 and 1120 shown in FIG. 11A. The PVT chart 1100 illustrates asphaltene phase as a function of pressure and composition, whereas the PVT chart 1120 illustrates asphaltene phase as a function of pressure and temperature.

Figure 11B:
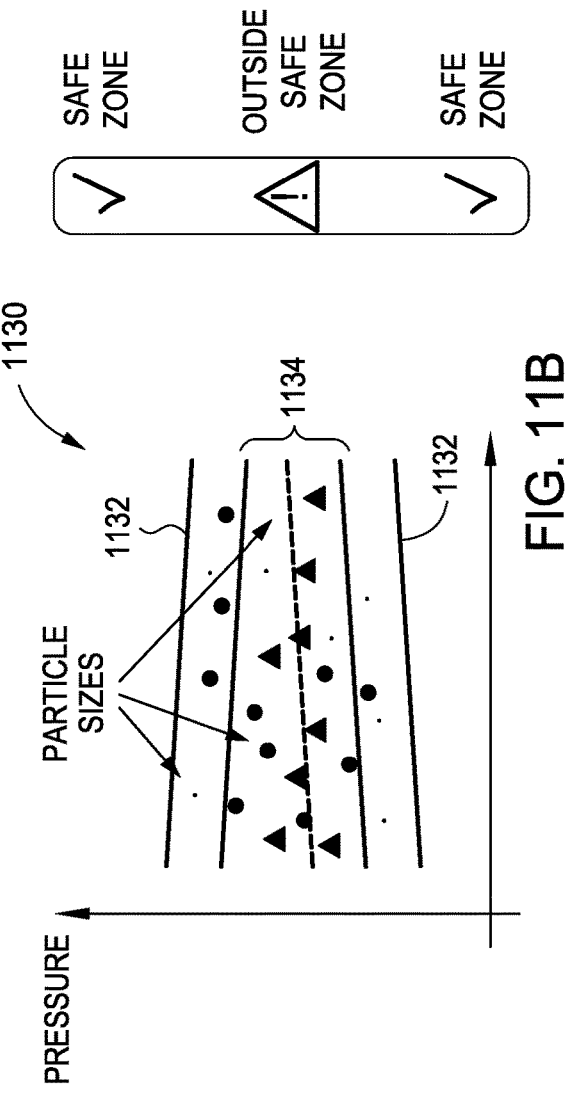
FIG. 11B is a plot of asphaltene particle sizes based on pressure, illustrating operational safe zones, in accordance with certain aspects of the present disclosure.

EPR may be used to measure various parameters, two of which are illustrated in the chart 1130 of FIG. 11B. These parameters may include, for example: (1) the total asphaltene regardless of particle size (i.e., bulk asphaltene); and (2) an envelope 1132 of the total dissolved particles (dots) to the envelope 1134 for the majority of the flocculated/large particles (triangles). Based on these two parameters, EPR can measure and help determine if a well or an area of a field stays inside the "safe" zones (above the upper boundary and below the lower boundary of envelope 1132). Operational condition(s) (e.g., pressure) and/or injection condition(s) may be adjusted in an effort to stay in the safe zones (e.g., according to the PVT charts 1100 and 1120). Once safe zone conditions are established, the EPR system may be used to monitor the well and avoid operation out of the safe zones.

Figure 12A:
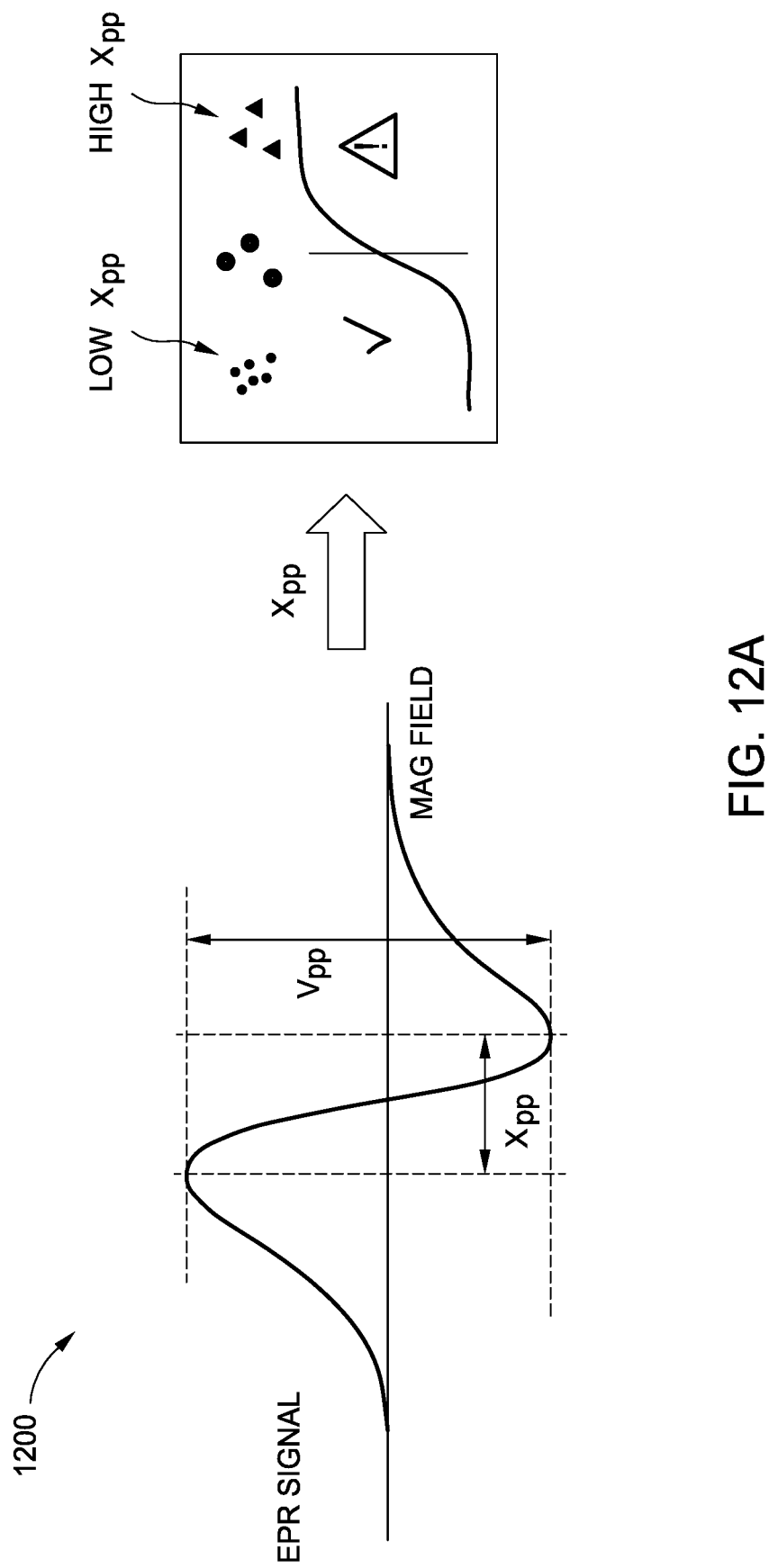
FIGS. 12A and 12B illustrate monitoring characteristics of a fluid based on an example EPR signal, in accordance with certain aspects of the present disclosure.

As shown in the plot 1200 of FIG. 12A, the shape of the EPR curve itself provides useful information. Babakhani '478 has disclosed that the height of the anomaly, $V_{pp}$, is indicative of the concentration of a paramagnetic component. The width of the anomaly, $X_{pp}$, (measured between points associated with the EPR signal peaks) is indicative of a relaxation time, also known as T2. Large particles will in general correspond to a broader anomaly (i.e., a higher $X_{pp}$). Consequently, by monitoring the line width, the EPR system may be used to provide a further indication that the conditions are moving out of the safe zone. More details on line-width analysis are given in Freed, J. H., et al., "Theory of Linewidths in Electron Spin Resonance Spectra," *The Journal of Chemical Physics*, vol. 39, (1963) p. 326.

Given the indication (e.g., represented as a check mark or a caution symbol) that the operation is moving out of the safe zones (e.g., with a wider $X_{pp}$), then operational condition(s) (e.g., pressure) and/or injection condition(s) may be adjusted in an effort to stay in the safe zones (e.g., according to the PVT charts 1100 and 1120). Once safe zone conditions are established, the EPR system may be used to monitor the well and avoid operation out of the safe zones.

Example EPR Monitoring Based on Change from a Baseline

Figure 12B:
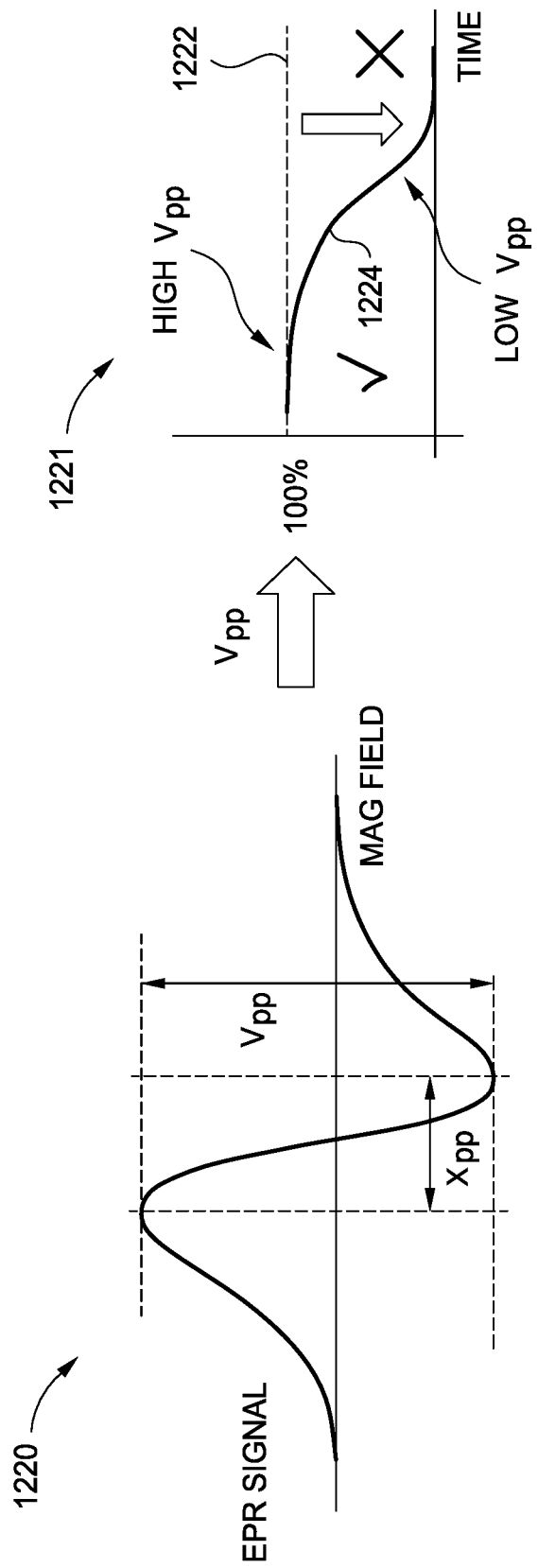

Other EPR monitoring techniques may prove to be more exact than monitoring the anomaly width, as explained above for FIG. 12A. The plot 1220 in FIG. 12B contains the same representative curve of EPR signal versus magnetic field as FIG. 12A, except that instead of deriving and using line width, the algorithm determines and utilizes the peak-to-peak voltage ($V_{pp}$). It is known that $V_{pp}$ correlates to asphaltene concentration. By taking a sample of crude oil and varying the percentage of asphaltene therein, it is possible to derive a specific correlation. Taking real-time data from an EPR sensor and converting to asphaltene percentage gives the chart 1221 illustrating deviation of a trace 1224 representing an asphaltene concentration in oil from a baseline value 1222 over time.

It is to be noted, however, that a calibration (such as the correlation calibration described above) is not mandatory. Instead, it may be sufficient to consider the deviation from baseline. In other words, when the oil tracks the baseline, then the oil is in the safe zone, but when the EPR signal drops, then that is indicative of less asphaltene. In this case, the signal may be flagged as being outside the safe zone.

Figure 13:
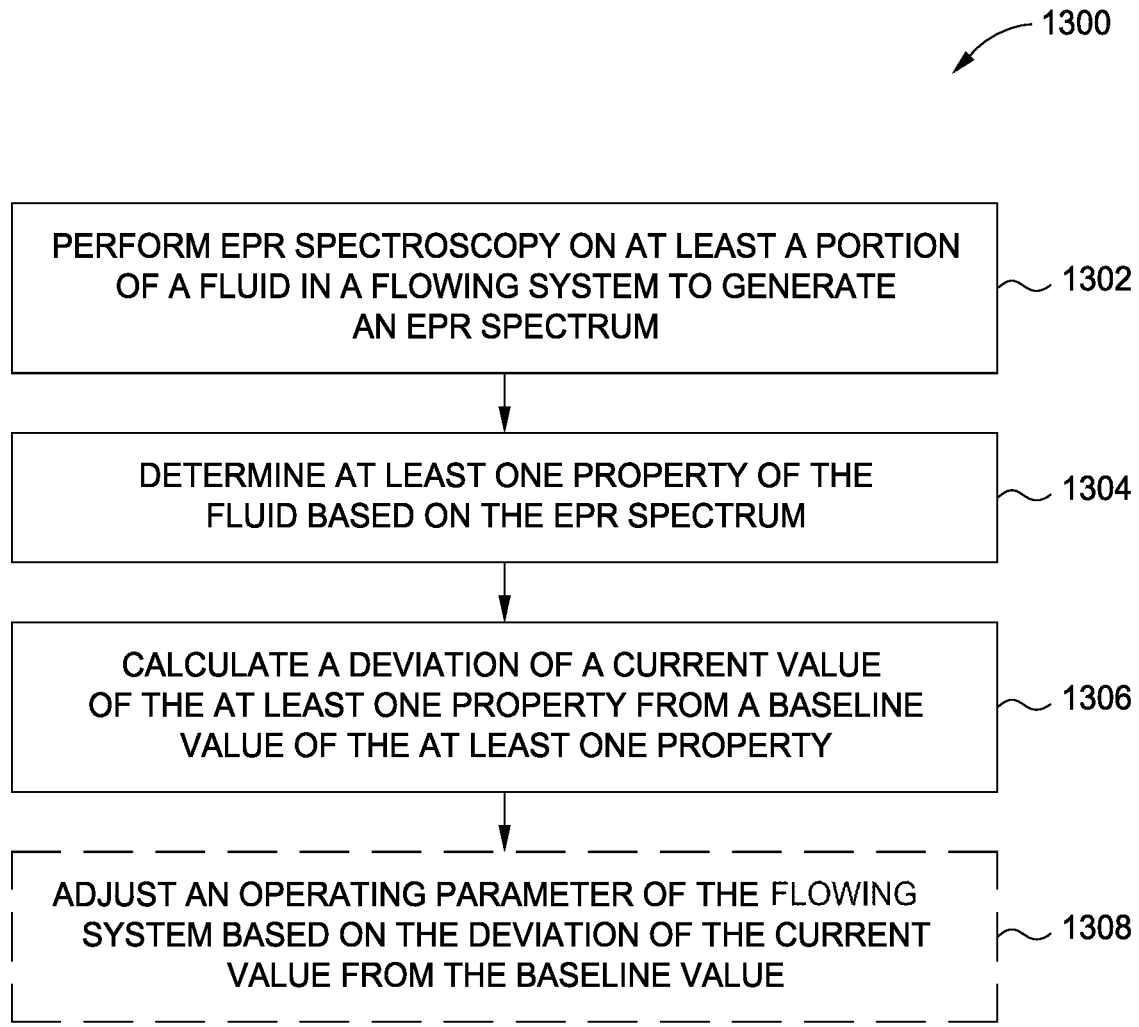
FIG. 13 is a flow diagram of example operations for sensing a fluid in a flowing system using EPR, in accordance with certain aspects of the present disclosure.

FIG. 13 is a flow diagram of example operations 1300 for sensing a fluid in a flowing system using EPR. The operations 1300 may begin, at block 1302, by performing EPR spectroscopy, using an EPR spectrometer, on at least a portion of the fluid to generate an EPR spectrum. At block 1304, at least one property of the fluid may be determined based on the EPR spectrum. At block 1306, a deviation of a current value of the at least one property from a baseline value of the at least one property may be calculated.

According to certain aspects, the operations 1300 may further involve, at optional block 1308, adjusting an operating parameter of the flowing system based on the deviation of the current value of the at least one property from the baseline value of the at least one property. For certain aspects, the operations 1300 may further include repeating the performing the EPR spectroscopy to generate an updated EPR spectrum, after the adjusting at optional block 1308, and identifying a change in the updated EPR spectrum from a previously generated EPR spectrum. For certain aspects, the operations 1300 may further entail repeating the performing at block 1302, the determining at block 1304, the calculating at block 1306, and the adjusting at optional block 1308 for automated closed-loop control of the operating parameter. For certain aspects, the operating parameter includes a rate or a volume of fluid injection into the flowing system. Additionally or alternatively, the operating parameter includes a pressure, a type, or a concentration of an injected fluid being introduced into the flowing system.

According to certain aspects, the baseline value was generated by: (1) repeating the performing at block 1302 and the determining at block 1304 over time to generate multiple values of the at least one property; and (2) deriving the baseline value based on the multiple values of the at least one property.

According to certain aspects, the flowing system includes a system for hydrocarbon recovery operations. In this case, the fluid may include oil. For certain aspects, the at least one property includes a concentration of asphaltene in the fluid or a concentration of asphaltene in the oil.

According to certain aspects, the flowing system comprises a system for hydrocarbon recovery operations including a wellhead. In this case, the performing at block 1302 may entail performing the EPR spectroscopy on the at least the portion of the fluid at or adjacent the wellhead.

According to certain aspects, the operations 1300 may further involve determining at least one electromagnetic attribute of the at least the portion of the fluid. In this case, determining the at least one property of the fluid at block 1304 may include determining the at least one property of the fluid based on the EPR spectrum and the at least one electromagnetic attribute. For certain aspects, determining the at least one electromagnetic attribute is based on performing the EPR spectroscopy. In this case, the at least one electromagnetic attribute may include at least one of a conductivity, a dielectric property, a magnetic susceptibility, or a magnetic permeability, of the at least the portion of the fluid.

According to certain aspects, the fluid comprises a multiphase fluid.

Example Asphaltene and Paraffin Flocculation and Precipitation

Figure 14:
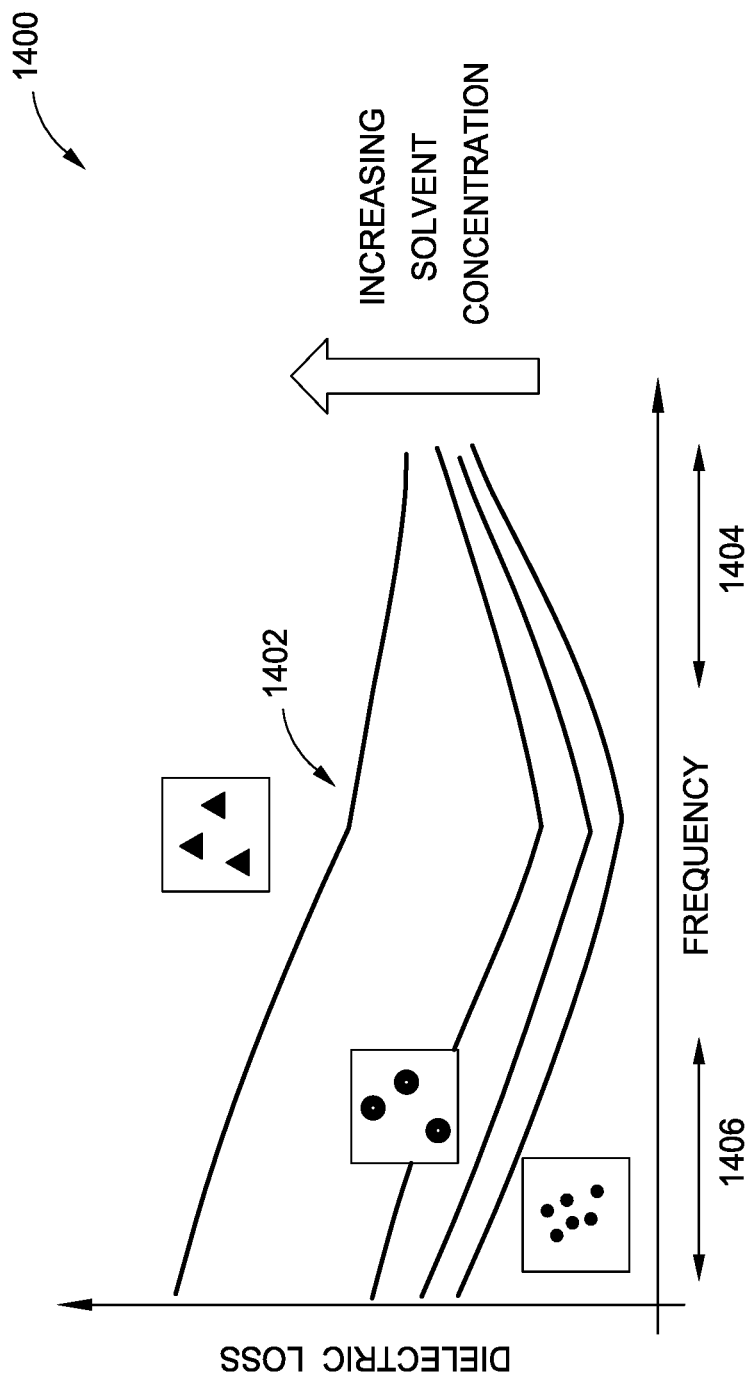
FIG. 14 is a plot of AC conductivity versus frequency as a function of asphaltene particle size, in accordance with certain aspects of the present disclosure.

In cases where the EPR sensor includes a complex permittivity measurement over a frequency range, the EPR system can identify flocculation by analyzing the change in that frequency measurement that occurs as the polar components coalesce. For a practical application, there may be too many parameters to fit a full mixing model. Instead, according to certain aspects, a series of baselines may be developed from a sample of fluid from the well that is targeted with increasing alkane (e.g., n-heptane). FIG. 14 is an example plot 1400 showing the variation of the imaginary component of permittivity (i.e., the dielectric loss) as a function of frequency. A frequency range has been chosen such that in the lower frequencies, the conductivity component will dominate, whereas as the frequency increases, then dipole relaxation will dominate. As the fluid enters into the warning "yellow" zone because of pressure or concentration changes, then the most polar components may coalesce, and flocculation may begin. This induces a change in the characteristic shape of the curve. For example, in FIG. 14, that characteristic is the presence of inflection point 1402 between the range of lower frequencies 1406 and the range of upper frequencies 1404.

Publications describing potential characteristics include Lesaint, C., et al., "Properties of Asphaltene Solutions: Solvency Effect on Conductivity," Energy Fuels, 27 (1), (2013), pp. 75-81; Goual, L., "Impedance of Petroleum Fluids at Low Frequency," Energy and Fuels, 23, (2009), pp. 2090-2094; Penzes, S., et al., "Electrical conductivities of bitumen fractions in non-aqueous solvents," Fuel, 53, (1974), pp. 192-197; Fotland, P., "Conductivity of Asphaltenes," *Structure and Dynamics of Asphaltenes*, Plenum: New York, 1998; Sheu, E. Y., et al., "Frequency-dependent conductivity of Utah crude oil asphaltene and deposit," Energy Fuels, 18, (2004), pp. 1531-1534; Sheu, E. Y., et al., "Asphaltene self-association and precipitation in solvents and AC conductivity measurements," *Asphaltenes, Heavy Oils and Petroleomics*, Springer: New York, 2007; and Sheu, E. Y., et al., "A dielectric relaxation study of precipitation and curing of Furrial crude oil," Fuel, vol. 85, (2006) pp. 1953-1959. All of these papers are herein incorporated by reference in their entireties.

Example operations for the technique may begin by taking a sample of oil (e.g., crude oil) and measuring EPR and dielectric spectral response for increasing alkane. A frequency range may be identified in which a conductivity component can be seen for lower frequencies and a dipole moment can be seen for higher frequencies (e.g., that the conductivity has a region of negative slope versus frequency and a second region of increasing slope). Optionally, a concentration of alkane indicated to remove the dipole moment may be identified (so that the AC conductivity is monotonic decreasing over the entire frequency range). The dielectric values versus frequency may be monitored in real-time, and an alert indication may be generated if the dipole moment drops. This may be combined with the EPR sensor to generate another alert indication for any change in the paramagnetic species of interest.

In the case of paraffin buildup, the component precipitating is nonpolar. However, field experience shows that the paraffin buildup will also precipitate out some of the polar asphaltene components, so the same operations should apply.

Certain aspects of the present disclose provide apparatus and methods to enhance the interpretation of EPR data of a fluid including polar components through the use of a measurement of complex permittivity as a function of varying frequency. These may involve determining at least one characteristic of the permittivity curve versus frequency that identifies a consolidation of the polar components.

Any of the operations described above, such as the operations 500, 600, 700, 800, 900, 1000, and/or 1300 may be included as instructions in a computer-readable medium for execution by a control unit (e.g., controller module 206) or any other processing system. The computer-readable medium may comprise any suitable memory for storing instructions, such as read-only memory (ROM), random access memory (RAM), flash memory, an electrically erasable programmable ROM (EEPROM), a compact disc ROM (CD-ROM), a floppy disk, and the like.

While the foregoing is directed to certain aspects of the present disclosure, other and further aspects may be devised without departing from the basic scope thereof, and the scope thereof is determined by the claims that follow.

What is claimed is:

1. A system for extracting hydrocarbon from a subterranean reservoir via a wellbore, comprising:
   an injector configured to inject fluid into the subterranean reservoir or the wellbore;
   a wellhead to control flow of produced fluid from the wellbore;
   a sensor configured to measure a property of a chemical species within or conveyed by the produced fluid; and
   at least one controller configured to analyze the property of the chemical species and to control the injector or the injected fluid based on the property of the chemical species.

2. The system of claim 1, further comprising a transmitter to convey data from the sensor in real-time to the at least one controller.

3. The system of claim 1, wherein the at least one controller is further configured to halt flow of the produced fluid while the injected fluid is allowed to soak in the subterranean reservoir.

4. The system of claim 3, wherein the sensor is further configured to measure properties of the produced fluid after well production recommences.

5. The system of claim 1, wherein the sensor is further configured to measure at least one of:
   a paramagnetic property of the produced fluid or the chemical species;
   an electromagnetic property of the produced fluid or the chemical species; or
   a property associated with an electron paramagnetic resonance (EPR) response of the produced fluid or the chemical species.

6. The system of claim 5, wherein the electromagnetic property comprises a conductivity, a complex dielectric value, a Q-factor, a magnetic susceptibility, a magnetic permeability, or a combination thereof.

7. The system of claim 1, wherein the chemical species comprises free radicals, metal ions, porphyrins, asphaltenes, resins, waxes, iron oxides, iron carbonates, iron sulfides, scale, injected tracers, or a combination thereof.

8. The system of claim 1, wherein the sensor comprises or is coupled to a chamber through which the produced fluid is configured to flow.

9. The system of claim 8, wherein the measured property is at least one of:

a paramagnetic property of the produced fluid or the chemical species within the chamber;

an electromagnetic property of the produced fluid or the chemical species within the chamber; or a property associated with an electron paramagnetic resonance (EPR) response of the produced fluid or the chemical species within the chamber.

10. The system of claim 1, wherein the at least one controller is further configured to establish a baseline level of the property.

11. The system of claim 10, wherein:
the sensor is configured to measure the property of the chemical species in real-time; and
the at least one controller is further configured to compare the real-time measured property against the baseline level of the property.

12. The system of claim 11, wherein the at least one controller is further configured to adjust at least one of one or more parameters of the injected fluid or one or more operating parameters of the injector, based on the comparison against the baseline level.

13. The system of claim 12, wherein the parameters of the injected fluid comprise a volume of chemicals injected, a volume of inhibitors injected, a type of the injected fluid, a concentration of the injected fluid, or a combination thereof.

14. The system of claim 12, wherein the operating parameters include a rate of the injected fluid, a pressure of the injected fluid, a temperature of the injected fluid, or a combination thereof.

15. The system of claim 1, wherein the injector is disposed in a different wellbore.

16. The system of claim 1, wherein the sensor comprises an electron paramagnetic resonance (EPR) sensor.

17. The system of claim 1, wherein the sensor is configured to sense a paramagnetic species within or conveyed by the produced fluid.

18. A system for extracting hydrocarbon from a subterranean reservoir via a wellbore, comprising:
means for injecting fluid into the subterranean reservoir or the wellbore;
means for controlling flow of produced fluid from the wellbore;
means for measuring a property of a chemical species within or conveyed by the produced fluid;
means for analyzing the property of the chemical species; and
means for controlling the means for injecting fluid based on the property of the chemical species.

19. The system of claim 18, further comprising means for transmitting data from the means for measuring the property in real-time to the means for analyzing the property.

20. The system of claim 18, wherein the means for controlling the means for injecting fluid is further configured to control halting a flow of produced fluid while the injected fluid is allowed to soak in the subterranean reservoir.

21. The system of claim 20, wherein the means for measuring the property is further configured to measure properties of the produced fluid after well production recommences.

22. The system of claim 18, wherein the means for measuring the property is further configured to measure at least one of:
a paramagnetic property of the produced fluid or the chemical species;
an electromagnetic property of the produced fluid or the chemical species; or
a property associated with an electron paramagnetic resonance (EPR) response of the produced fluid or the chemical species.

23. The system of claim 22, wherein the electromagnetic property comprises a conductivity, a complex dielectric value, a Q-factor, a magnetic susceptibility, a magnetic permeability, or a combination thereof.

24. The system of claim 18, wherein the chemical species comprises free radicals, metal ions, porphyrins, asphaltenes, resins, waxes, iron oxides, iron carbonates, iron sulfides, scale, injected tracers, or a combination thereof.

25. The system of claim 18, wherein the means for measuring the property comprises or is coupled to a chamber through which the produced fluid is configured to flow.

26. The system of claim 25, wherein the measured property is at least one of:
a paramagnetic property of the produced fluid or the chemical species within the chamber;
an electromagnetic property of the produced fluid or the chemical species within the chamber; or
a property associated with an electron paramagnetic resonance (EPR) response of the produced fluid or the chemical species within the chamber.

27. The system of claim 18, wherein the means for analyzing the property is further configured to establish a baseline level of the property.

28. The system of claim 27, wherein:
the means for measuring the property is configured to measure the property of the chemical species in real-time; and
the means for analyzing the property is further configured to compare the real-time measured property against the baseline level of the property.

29. The system of claim 28, wherein the means for controlling the means for injecting fluid is further configured to control adjusting at least one of one or more parameters of the injected fluid or one or more operating parameters of the means for injecting fluid, based on the comparison against the baseline level.

30. The system of claim 29, wherein the parameters of the injected fluid comprise a volume of chemicals injected, a volume of inhibitors injected, a type of the injected fluid, a concentration of the injected fluid, or a combination thereof.

31. The system of claim 29, wherein the operating parameters include a rate of the injected fluid, a pressure of the injected fluid, a temperature of the injected fluid, or a combination thereof.

32. A method for extracting hydrocarbons from a subterranean reservoir via a wellbore, comprising:
measuring, with a sensor, a baseline value of a property of a chemical species within or conveyed by a fluid in a flowing system;
injecting an injection fluid into the subterranean reservoir or the wellbore;
measuring a change in the property of the chemical species from the baseline value of the property after injecting the injection fluid; and
adjusting a parameter of the flowing system based on the change in the property of the chemical species.

33. The method of claim 32, further comprising measuring a second baseline value of the fluid after adjusting the parameter of the flowing system.

34. The method of claim 32, wherein the method further comprises performing an intervention, scraping tubing walls allowing the injection fluid to soak, changing an injection rate, changing the injection fluid injected, changing a wellhead pressure, or a combination thereof.

35. The method of claim 32, further comprising halting a flow of the fluid while the injected fluid soaks in the subterranean reservoir.

36. The method of claim 32, wherein the measured change in the property of the chemical species is a change in a paramagnetic property of the chemical species, an electromagnetic property of the chemical species, a property associated with an electron paramagnetic resonance (EPR) response of the chemical species, or a combination thereof.

37. The method of claim 36, wherein the electromagnetic property comprises a conductivity, a complex dielectric value, a Q-factor, a magnetic susceptibility, a magnetic permeability, or a combination thereof.

38. The method of claim 32, wherein the chemical species comprises free radicals, metal ions, porphyrins, asphaltenes, resins, waxes, iron oxides, iron carbonates, iron sulfides, scale, injected tracers, or a combination thereof.

* * * * *